United States Patent [19]

Foley et al.

[11] 3,931,266

[45] Jan. 6, 1976

[54] ORGANO SILICON COMPOUNDS

[75] Inventors: Kevin M. Foley, Hebron; Francesco M. Vigo, Heath, both of Ohio

[73] Assignee: Owens-Corning Fiberglas Corporation, Toledo, Ohio

[22] Filed: Apr. 2, 1973

[21] Appl. No.: 347,241

[52] U.S. Cl. ............ 260/448.8A; 260/448.8R; 260/348 SC; 117/124 F
[51] Int. Cl.² ................ C07F 7/04; C07F 7/18
[58] Field of Search ........... 260/448.8 A, 448.8 R

[56] References Cited
UNITED STATES PATENTS

| | | | |
|---|---|---|---|
| 2,511,013 | 6/1950 | Rust et al. | 260/448.8 A X |
| 2,529,956 | 11/1950 | Myles et al. | 260/448.8 A X |
| 3,555,051 | 1/1971 | Marsden et al. | 260/448.8 A X |

*Primary Examiner*—Paul F. Shaver
*Attorney, Agent, or Firm*—Carl G. Staelin; John W. Overman; Keith V. Rockey

[57] ABSTRACT

This invention is addressed to organo silicon compounds prepared by reaction of a halosilane, a monoepoxide containing at least one other functional group, and at least one polyepoxide. The products of this invention are liquid organo silicon compounds which are useful in the treatment of glass fibers to improve the bonding relationship between glass fibers and resinous or elastomeric materials.

20 Claims, No Drawings

ORGANO SILICON COMPOUNDS

This invention relates to organo silicon compounds, and more particularly to complex organo silicon compounds which are resistant to hydrolysis.

Organo silicon compounds have found widespread use in a variety of applications and have been found to be particularly well suited for use in the treatment of highly hydrophilic substrates, such as glass and glass fibers, to render the hydrophilic substrates more compatible with hydrophobic systems. Thus, in the manufacture of glass fiber reinforced plastics and glass fiber reinforced elastomeric products such as drive belts, rubber tires and the like, it has been the practice to treat the glass fibers with organo silicon compounds.

The organo silicon compounds frequently used for this purpose are the organo silanes of the formula $$R\text{-}Si(OR')_3 \quad (1)$$

wherein R is an organic group which may contain any of a variety of functional groups, such as amino, epoxy, hydroxy, mercapto, etc., and R' is an alkyl group. While such silanes as well as their hydrolysis products and polymerization products are quite effective in promoting a secure bonding relationship between glass fibers and resins and elastomeric materials, they are nevertheless expensive to manufacture and consequently contribute to the overall costs in the manufacture of glass fiber reinforced resins and elastomeric materials.

It is known, as shown by U.S. Pat. No. 2,650,934, that an alkylene oxide can be reacted with silicon tetrahalides such as silicon tetrachloride as follows:

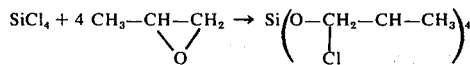
(2)

While this reaction is known, it has only recently been discovered that the tetrakis alkoxy silane produced is stable in aqueous media against hydrolysis. Without limitation as to theory, it is believed that the halogen atom in the beta-position serves to stabilize the bond between the alkoxy group and the silicon atom.

It has also been suggested that silanized epoxide resins can be prepared by reaction of an epoxide resin with an organo silane in the presence of an amine. In this reaction, which is disclosed in U.S. Pat. No. 3,169,884, the product does not contain the stabilized

(3)

group.

It is an object of the present invention to produce complex organo silicon compounds which contain beta-haloalkoxy groups attached directly to the silicon atoms which stabilize the compounds against hydrolysis.

It is a more specific object of this invention to produce organo silicon compounds which contain highly reactive functional groups along with beta-haloalkoxy groups for use in the treatment of highly hydrophilic substrates to render such substrates more hydrophobic.

The concepts in this invention reside in complex organo silicon compounds which are prepared by reaction of a halosilane with at least one monoepoxide and at least one polyepoxide. As will be appreciated by those skilled in the art, the nature of the product depends not only upon the specific combination of epoxides employed but also upon the reactant proportions. In all cases, however, the reaction product includes a mixture of compounds which can be utilized as such, or, if desired, the predominant compounds forming the reaction product can be separated in relatively pure form.

As the monoepoxide, use is preferably made of organic epoxides containing at least one other functional group. By way of illustration, the following compounds can be employed: Epoxides of the formula

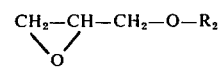
(4)

wherein $R_2$ is an aryl group and preferably phenyl or phenyl substituted with an amino group, a halogen group, an alkyl group; alkyl containing 1 to 20 carbon atoms and substituted derivatives thereof; an alkenyl group containing 2 to 8 carbon atoms (e.g., vinyl, allyl, etc.); a group having the formula

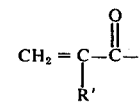
(5)

wherein R' is hydrogen or methyl. Illustrative of such epoxides are phenyl glycidyl ether, cresyl glycidyl ether, allyl glycidyl ether, glycidyl acrylate, glycidyl methacrylate, a mixture of n-octyl and n-decyl glycidyl ether (Epoxide No. 7 from Procter and Gamble) and a mixture of n-dodecyl and n-tetradecyl glycidyl ethers (Epoxide No. 8 from Procter and Gamble).

As the polyepoxide, use is preferably made of diepoxide, such as the following epoxides of the formula

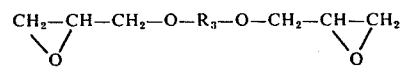
(6)

wherein $R_3$ is a divalent organic radical such as alkylene containing 1 to 10 carbon atoms; alkyleneoxyalkylene containing 2 to 20 carbon atoms; divalent aromatic groups such as a group of the formula

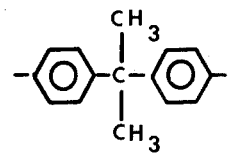
(7)

or

(8)

A number of such epoxides are commercially available from Dow and Ciba and include the following:

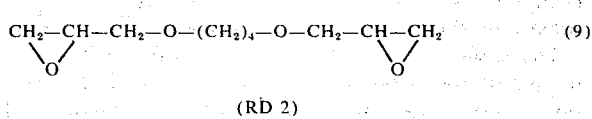 (9)

(RD 2)

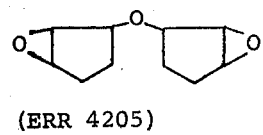 (16)

(ERR 4205)

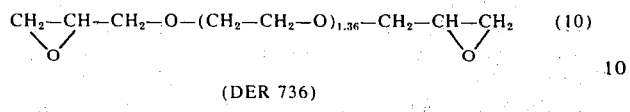 (10)

(DER 736)

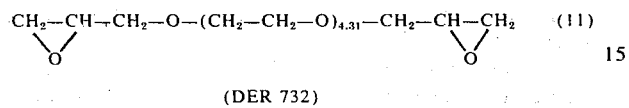 (11)

(DER 732)

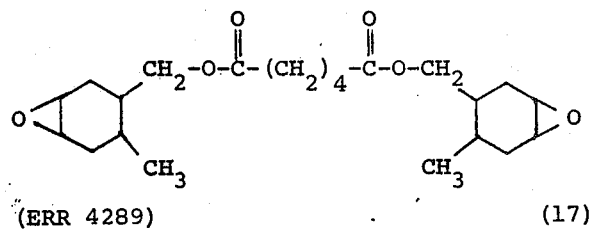 (17)

(ERR 4289)

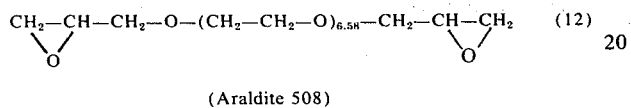 (12)

(Araldite 508)

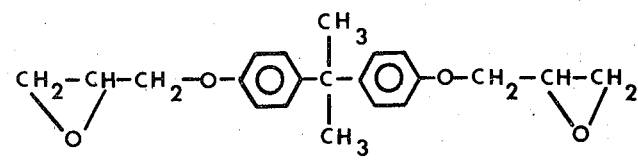

(DER 332)

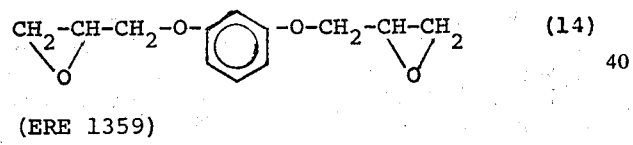 (14)

(ERE 1359)

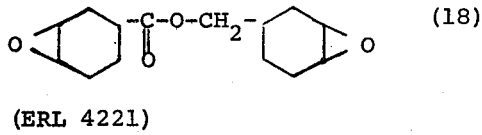 (18)

(ERL 4221)

Cycloalkane epoxides, including the following:

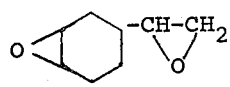

(RD 4 or ERL 4206) (15)

In accordance with one embodiment of the invention, the organo silicon compounds are prepared by reaction of from 1 to 3 epoxide equivalents of the monoepoxide and at least 0.5 and up to 3 epoxide equivalents of another epoxide containing a functional group per mole of the silicon tetrahalide. As used herein, the term "epoxide equivalent" refers to the number of moles of the epoxide divided by the number of epoxide groups per molecule.

For example, use can be made of a monoepoxide containing another functional group and a diepoxide as described above. This reaction can be illustrated by way of the following equations:

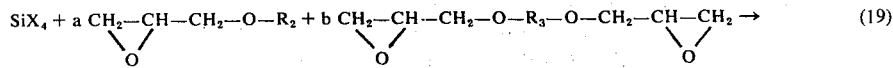 (19)

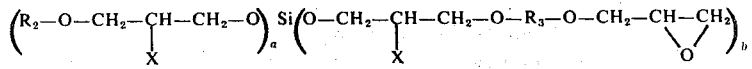

and

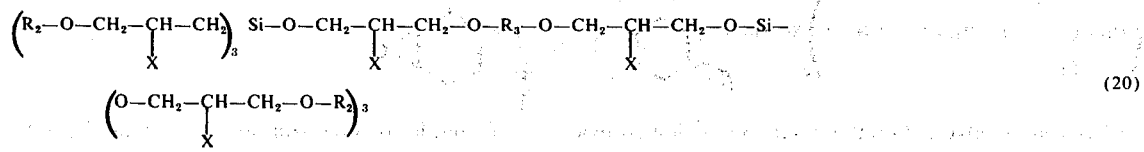

(20)

wherein X represents halogen, a represents the epoxide equivalent of the monoepoxide and b represents the epoxide equivalent of the diepoxide. In actual practice, the reaction product produced is a mixture of compounds which can be utilized as such without the need to separate specific compounds contained in the reaction product.

However, compounds contained in the reaction mixture can be, if desired, separated from the mixture by known techniques such as fractional distillation, liquid chromatography, etc., to yield substantially pure compounds.

It has been found that in the reaction mixture, a should be at least 2.2, and preferably at least 2.5, to avoid polymer formation which causes gelling of the product. Thus, a is within the range of 2.2 to 3.5 and b is within the range of 0.5 to 1.8. It has also been found that where the reaction mixture contains 2 or more epoxide equivalents of the diepoxide, the compounds which predominate in the reaction mixture have the general formula

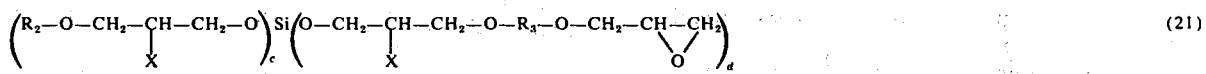

(21)

wherein c is within the range of 2.0 to 3 and d is within the range of 1 to 2.0. Most frequently c is 3 and d is 1.

Examples of specific compounds which can be prepared in accordance with this embodiment of the invention are:

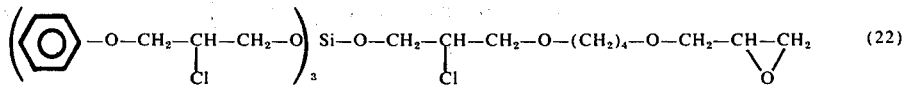

(22)

(SiCl$_4$ 1 mole; phenyl glycidyl ether 3 epoxide equivalents; RD 2 2 epoxide equivalents)

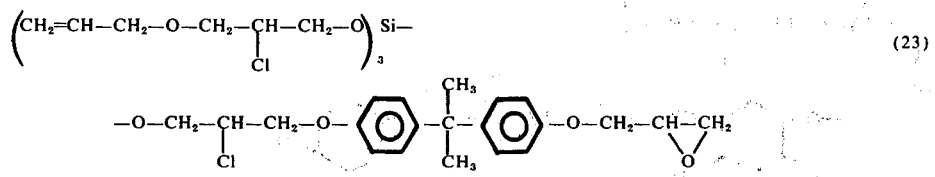

(23)

(SiCl$_4$ 1 mole; allyl glycidyl ether 3 epoxide equivalents; DER 332 2 epoxide equivalents)

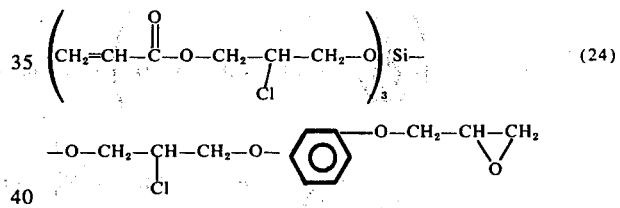

(24)

(SiCl$_4$ 1 mole; glycidyl acrylate 3 epoxide equivalents; ERE 1359 2 epoxide equivalents)

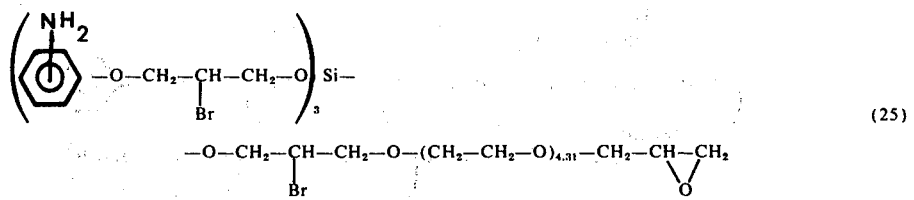

(25)

(SiBr$_4$ 1 mole; aminophenyl glycidyl ether 3 epoxide equivalents; DER 732 2 epoxide equivalents)

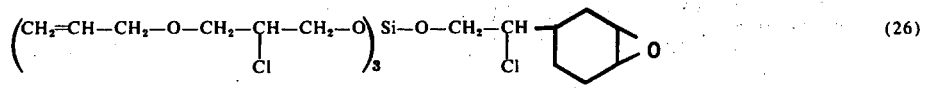

(26)

(SiCl$_4$ 1 mole; allyl glycidyl ether 1 epoxide equivalent; RD 4 2 epoxide equivalents)

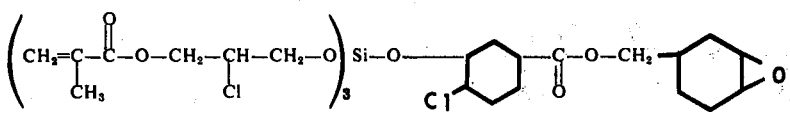
(27)

(SiCl$_4$ 1 mole; glycidyl methacrylate 3 epoxide equivalents; ERR 4221 2 epoxide equivalents)

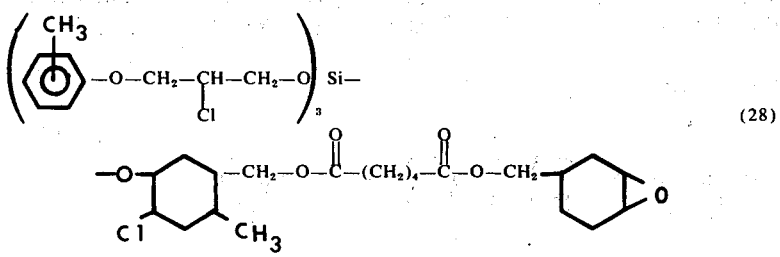

(SiCl$_4$ 1 mole; cresyl glycidyl ether 3 epoxide equivalents; ERR 4289 2 epoxide equivalents)

Where, however, use is made of less than 2 epoxide equivalents of the diepoxide, the product of the reaction includes compounds containing no free epoxy groups; these compounds have the general formula

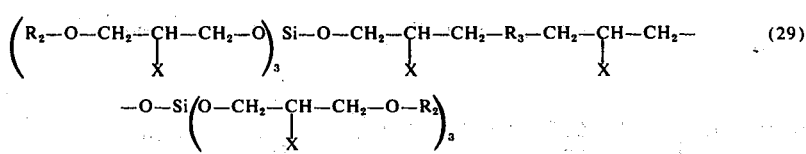
(29)

Examples of such compounds include the following:

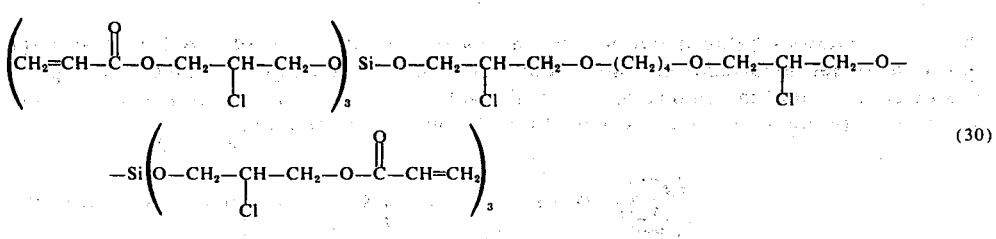
(30)

(SiCl$_4$ 1 mole; glycidyl acrylate 3 epoxide equivalents; RD 2 1 epoxide equivalent)

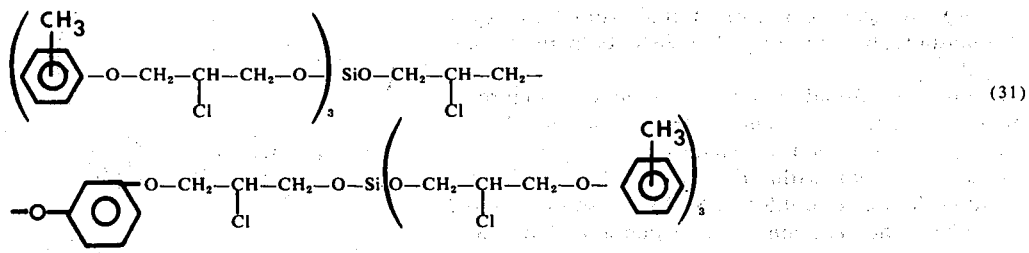
(31)

(SiCl$_4$ 1 mole; cresyl glycidyl ether 3 epoxide equivalents; ERE 1359 1 epoxide equivalent)

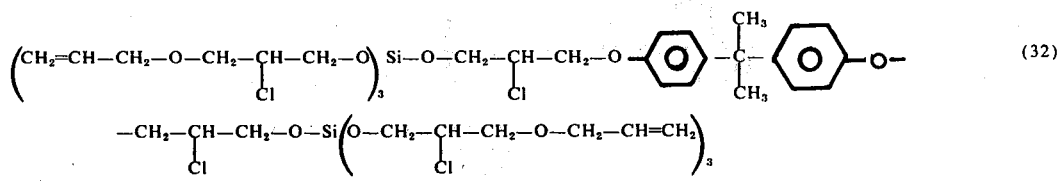
(32)

(SiCl$_4$ 1 mole; allyl glycidyl ether 3 epoxide equivalents; DER 332 1 epoxide equivalent)

-continued $$\left(C_{10}H_{21}-O-CH_2-\underset{Br}{CH}-CH_2-O\right)_3 Si-O-CH_2-\underset{Br}{CH}-CH_2-O-\left(CH_2-CH_2-O\right)_{6.58} \quad (33)$$

$$-CH_2-\underset{Br}{CH}-CH_2-O-Si\left(C_{10}H_{21}-O-CH_2-\underset{Br}{CH}-CH_2-O\right)_3$$

(SiBr$_4$ 1 mole; decyl glycidyl ether 3 epoxide equivalents; Araldite 508 1 epoxide equivalent)

As indicated above, styrene oxides as well as substituted derivatives thereof can also be used in the practice of this invention as the monoepoxide. Compounds produced in the reaction product thus have the formula $$\left(\phenyl-O-CH_2-\underset{Cl}{CH}-CH_2-O\right)_3 Si-O-\underset{Cl}{\bigcirc}-\overset{O}{\underset{\|}{C}}-O-CH_2-\bigcirc_{Cl}-O-Si- \quad (34)$$

$$-\left(O-CH_2-\underset{Cl}{CH}-CH_2-O-\phenyl\right)_3$$

(SiCl$_4$ 1 mole; phenyl glycidyl ether 3 epoxide equivalents; ERR 4221 1 epoxide equivalent)

$$\left(CH_2=\underset{CH_3}{\overset{}{C}}-\overset{O}{\underset{\|}{C}}-O-CH_2-\underset{Cl}{CH}-CH_2-O\right)_3 Si-O-\underset{Cl}{\bigcirc}-CH-CH_2-O-Si- \quad (35)$$

$$-\left(O-CH_2-\underset{Cl}{CH}-CH_2-O-\overset{O}{\underset{\|}{C}}-\underset{CH_3}{\overset{}{C}}=CH_2\right)_3$$

(SiCl$_4$ 1 mole; glycidyl methacrylate 3 epoxide equivalents; RD 4 1 epoxide equivalent)

$$\left(CH_2=CH-CH_2-O-CH_2-\underset{Cl}{CH}-CH_2-O\right)_3 Si-O-\underset{Cl}{\bigcirc}-CH_2-O-\overset{O}{\underset{\|}{C}}-(CH_2)_4-\overset{O}{\underset{\|}{C}}-O-CH_2-\bigcirc_{Cl}-O-Si-$$

$$-\left(O-CH_2-\underset{Cl}{CH}-CH_2-O-CH_2-CH=CH_2\right)_3 \quad (36)$$

(SiCl$_4$ 1 mole; allyl glycidyl ether 3 epoxide equivalents; ERR 4289 1 epoxide equivalent)

Representative compounds derivated from styrene oxide and a diepoxide include the following:

$$\left(\phenyl-\underset{X}{CH}-CH_2-O\right)_3 Si-O-CH_2-\underset{X}{CH}-CH_2-R_3-CH_2-CH-CH_2 \quad (37)$$
$$\overset{\diagdown O \diagup}{}$$

and/or $$\left(\phenyl-\underset{X}{CH}-CH_2-O\right)_3 Si-O-CH_2-\underset{X}{CH}-CH_2-R_3-CH_2-\underset{X}{CH}-CH_2-O-Si\left(O-CH_2-\underset{X}{CH}-\phenyl\right)_3 \quad (38)$$

$$\left(\phenyl-\underset{Cl}{CH}-CH_2-O\right)_3 Si-O-CH_2-\underset{Cl}{CH}-CH_2-O-\phenyl-O-CH_2-CH-CH_2 \quad (39)$$
$$\overset{\diagdown O \diagup}{}$$

(SiCl$_4$ 1 mole; styrene oxide 3 epoxide equivalents; ERE 1359 2 epoxide equivalents)

$$\left(\phenyl-\underset{Br}{CH}-CH_2-O\right)_3 Si-O-CH_2-\underset{Br}{CH}-CH_2-O-\phenyl-\underset{\underset{CH_3}{|}}{\overset{\overset{CH_3}{|}}{C}}-\phenyl-O-CH_2-CH-CH_2 \quad (40)$$
$$\overset{\diagdown O \diagup}{}$$

(SiBr₄ 1 mole; styrene oxide 3 epoxide equivalents; DER 332 1 epoxide equivalent)

(SiCl₄ 1 mole; styrene oxide 3 epoxide equivalents; RD 10 4 2 epoxide equivalents)

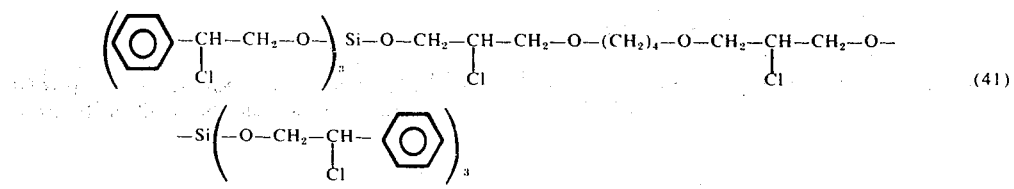
(41)

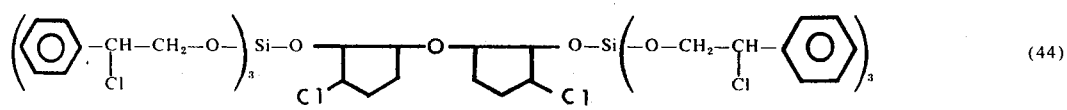
(44)

(SiCl₄ 1 mole; styrene oxide 3 epoxide equivalents; ERR 4205 1 epoxide equivalent)

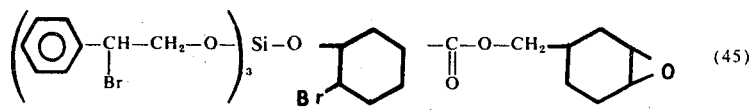
(45)

(SiCl₄ 1 mole; styrene oxide 3 epoxide equivalents; RD 2 1 epoxide equivalent)

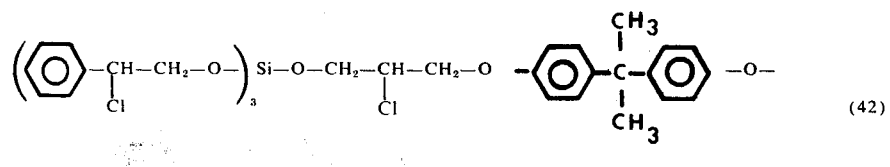
(42)

(SiBr₄ 1 mole; styrene oxide 3 epoxide equivalents; ERL 4221 2 epoxide equivalents)

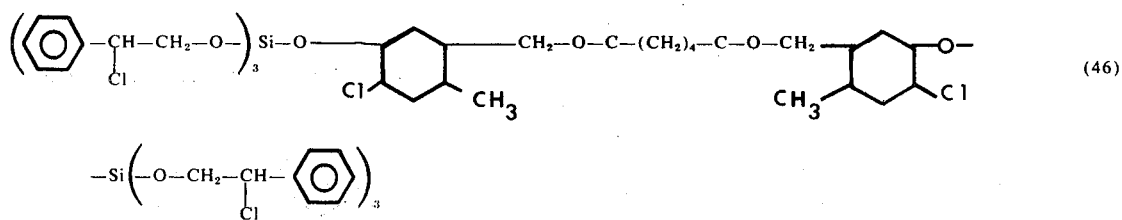
(46)

(SiCl₄ 1 mole; styrene oxide 3 epoxide equivalents; ERE 1359 1 epoxide equivalent)

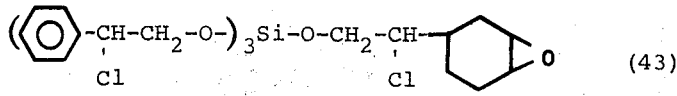
(43)

(SiCl₄ 1 mole; styrene oxide 3 epoxide equivalents; ERL 4289 1 epoxide equivalent)

In preparing the reaction mixtures of the present invention, the reactants are contacted in the liquid phase. An inert organic solvent can be employed, if desired, but is not essential to the practice of the invention. The reaction temperature is not critical as the reaction generally takes place spontaneously and evolves heat. Best results are usually achieved when the reaction temperature is maintained below 100°C such as within the range of 0° to 100°C.

In accordance with another concept of the present invention, the reaction is carried out with 0.5 to 2 moles of an alkylene oxide in addition to the monoepoxide and the diepoxide. In this embodiment of the invention, the alkylene oxide reacts with the halosilane in a similar manner to form a beta-haloalkoxy group attached directly to the silicon atom. This reaction can proceed in two ways, depending upon the amount of diepoxide employed. Thus, where the amount of the diepoxide is less than 2 epoxide equivalents, the reaction proceeds as follows:

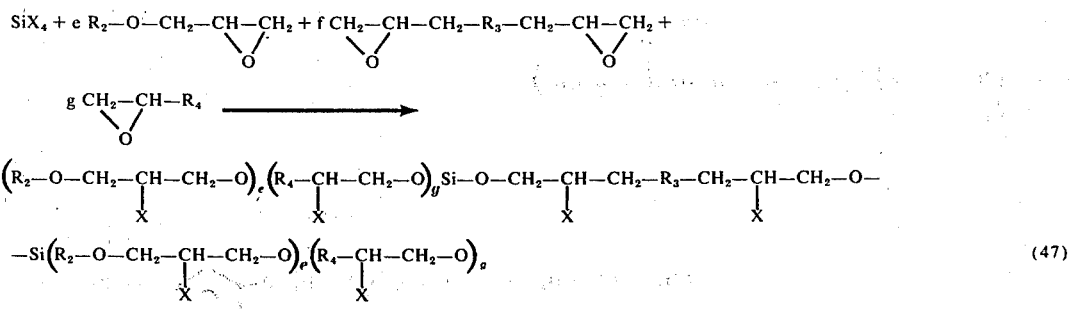

It is frequently preferred that the monoepoxide be added to the reaction mixture. This procedure has the advantage that the reaction of monoepoxide with the silicon tetrahalide is quite exothermic and thus raises the temperature of the reaction medium to a level suitable for addition of the diepoxide.

It will be observed that in all of the compounds specifically described above, each bond to the silicon atom contains a beta-haloalkoxy group. As indicated above, where $e$ and $g$ are each integers from 1 to 2 and $f$ is 1, and R is hydrogen or $C_1$ to $C_6$ alkyl (e.g., methyl, ethyl, propyl, etc.).

As with the embodiment described above, the reaction product of the above is a mixture which can be used as such or, if desired, the predominant compounds having the formula represented by (47) can be separated from the reaction mixture.

Examples of such compounds include the following:

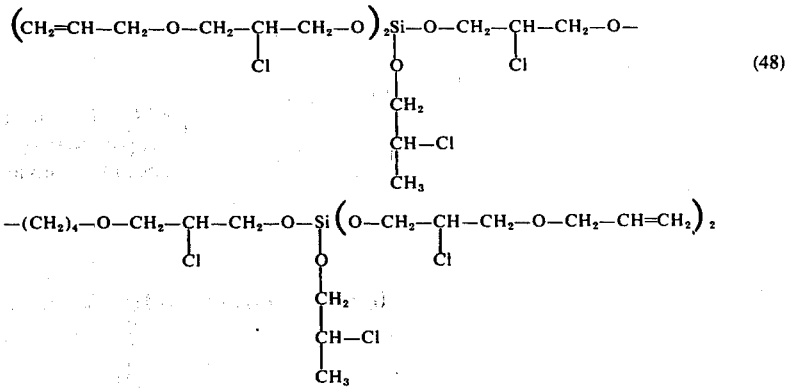

it is believed that such groupings impart improved stability to the compounds of the invention.

(SiCl₄ 1 mole; allyl glycidyl ether 2 epoxide equivalents; propylene oxide 1 epoxide equivalent; RD 2 1 epoxide equivalent)

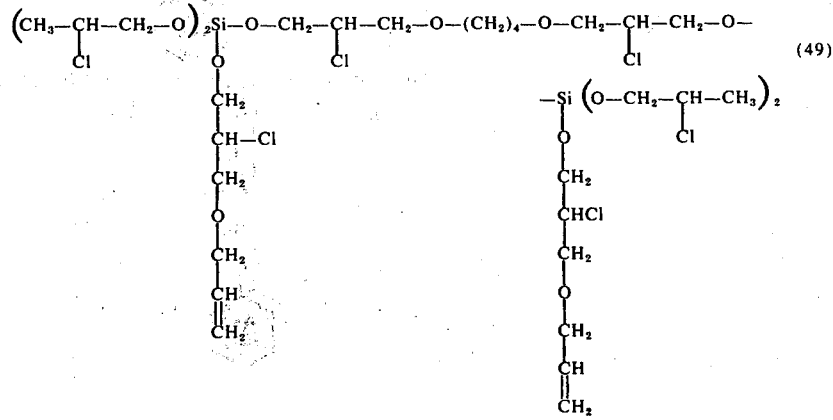

(SiCl₄ 1 mole; allyl glycidyl ether 1 epoxide equivalent; propylene oxide 2 epoxide equivalents; RD 2 1 epoxide equivalent)
(SiCl₄ 1 mole; glycidyl acrylate 2 epoxide equivalents; ethylene oxide 1 epoxide equivalent; ERE 1359 1 epoxide equivalent)
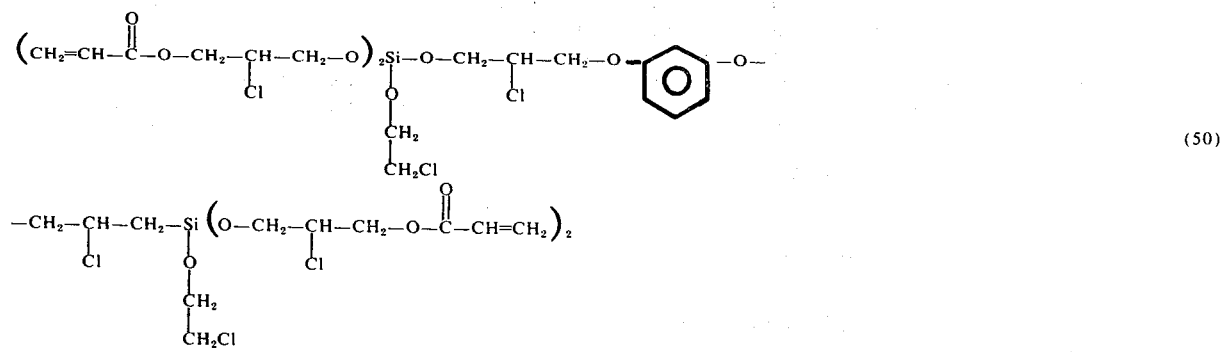
(50)
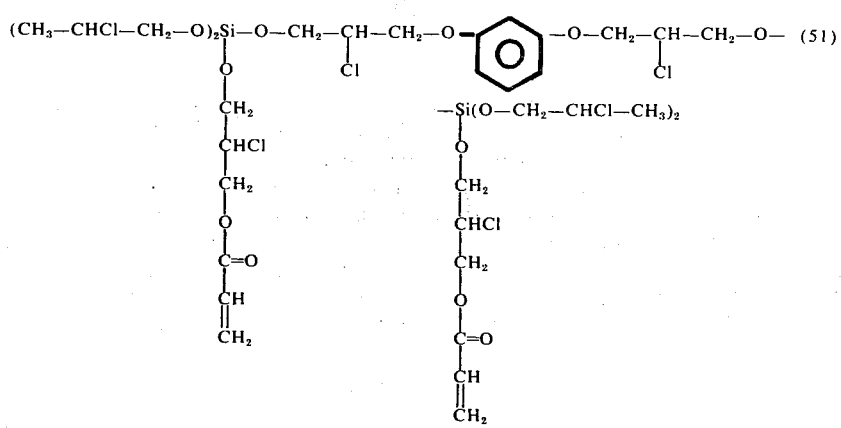
(51)
(SiCl₄ 1 mole; glycidyl acrylate 1 epoxide equivalent; propylene oxide 2 epoxide equivalents; ERE 1359 1 epoxide equivalent)
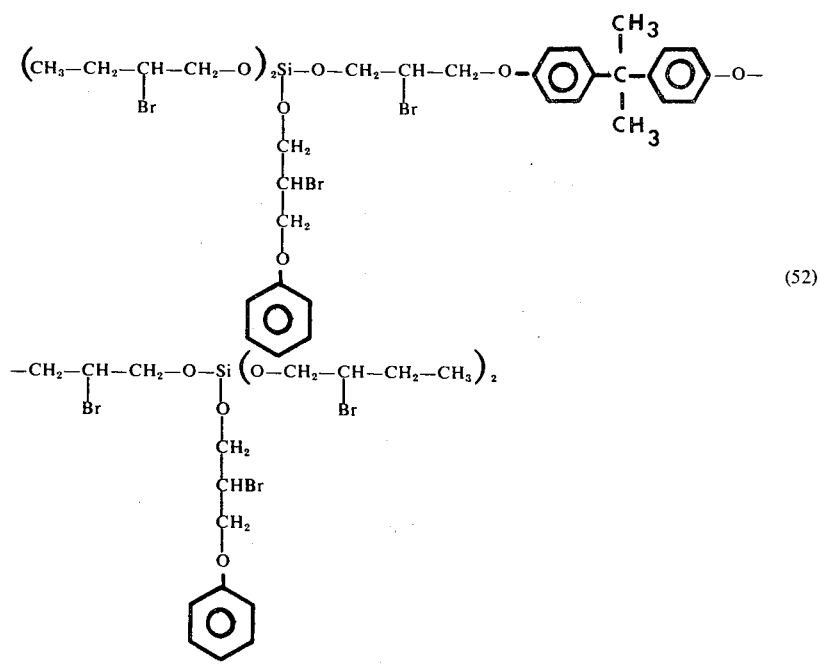
(52)

(SiBr₄ 1 mole; phenyl glycidyl ether 2 epoxide equivalents; butylene oxide 1 epoxide equivalent; DER 332 1 epoxide equivalent)

(SiCl₄ 1 mole; allyl glycidyl ether 1 epoxide equivalent; propylene oxide 2 epoxide equivalents; ERR 4289 1 epoxide equivalent)

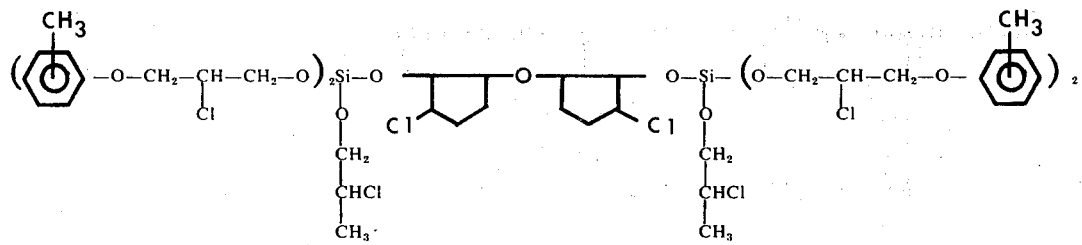

(53)

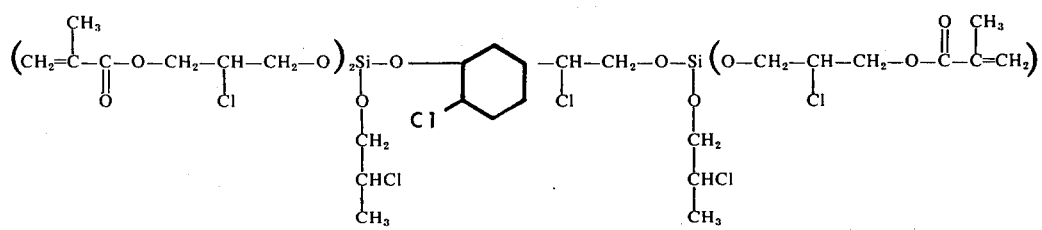

(55)

(SiCl₄ 1 mole; cresyl glycidyl ether 2 epoxide equivalents; propylene oxide 1 epoxide equivalent; ERR 4205 1 epoxide equivalent)

(SiCl₄ 1 mole; glycidyl methacrylate 2 epoxide equivalents; propylene oxide 1 epoxide equivalent; RD 4 1 epoxide equivalent)

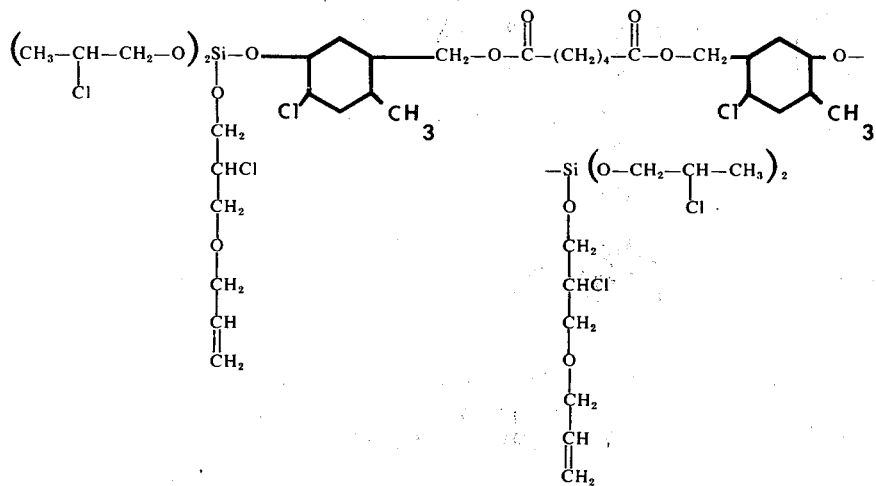

(54)

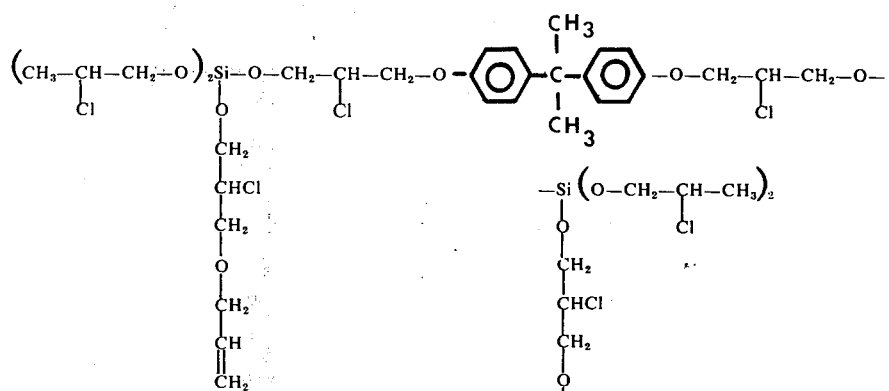

(56)

(SiCl₄ 1 mole; allyl glycidyl ether 1 epoxide equivalent; propylene oxide 2 epoxide equivalents; DER 332 1 epoxide equivalent)
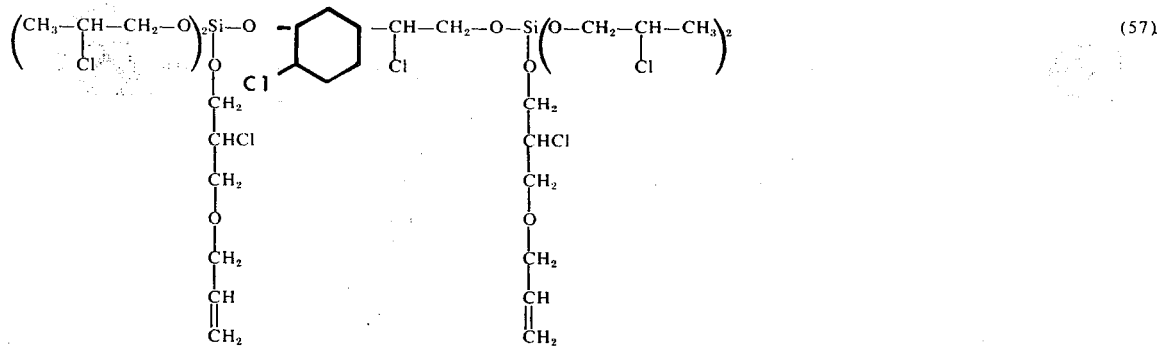
(57)
(SiCl₄ 1 mole; allyl glycidyl ether 1 epoxide equivalent; propylene oxide 2 epoxide equivalents; ERL 4206 1 epoxide equivalent)
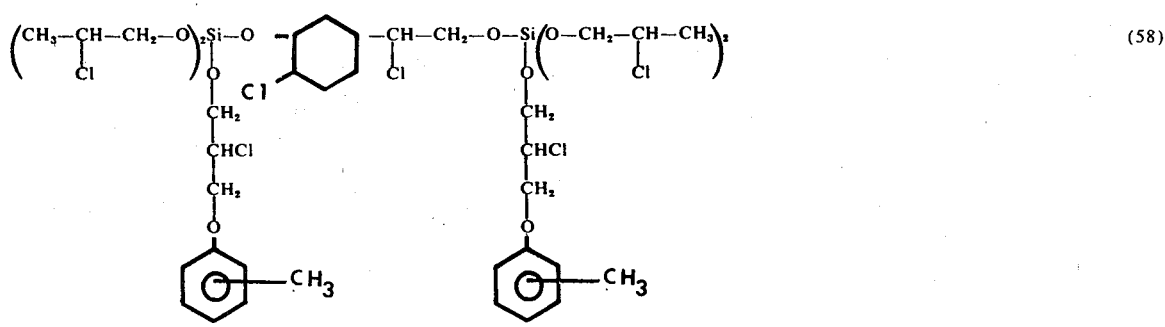
(58)
(SiCl₄ 1 mole; cresyl glycidyl ether 1 epoxide equivalent; propylene oxide 2 epoxide equivalents; ERL 4206 1 epoxide equivalent)
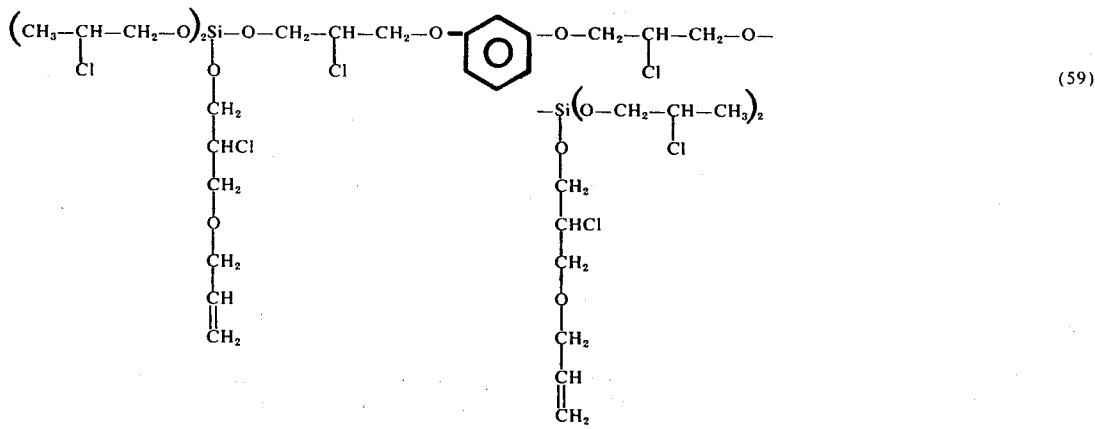
(59)

(SiCl₄ 1 mole; allyl glycidyl ether 1 epoxide equivalent; propylene oxide 2 epoxide equivalents; ERE 1359 1 epoxide equivalent)
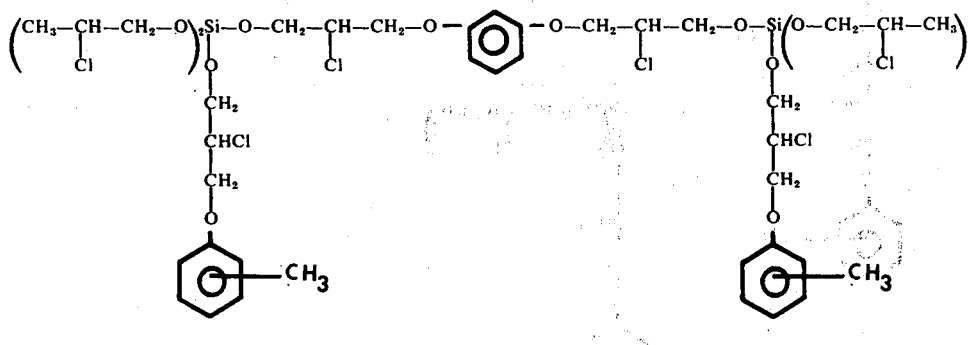
(60)
(SiCl₄ 1 mole; cresyl glycidyl ether 1 epoxide equivalent; propylene oxide 2 epoxide equivalents; ERE 1359 1 epoxide equivalent)
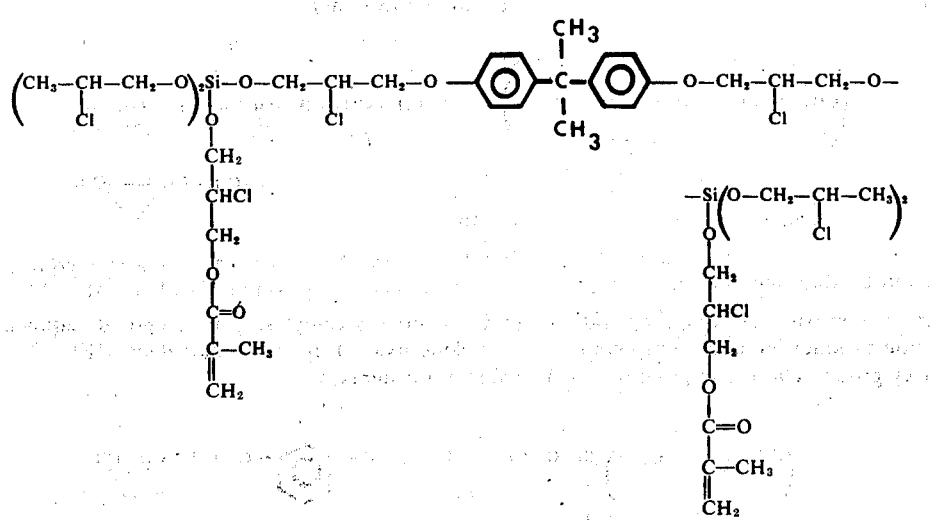
(61)
(SiCl₄ 1 mole; glycidyl methacrylate 1 epoxide equivalent; propylene oxide 2 epoxide equivalents; DER 332 1 epoxide equivalent)
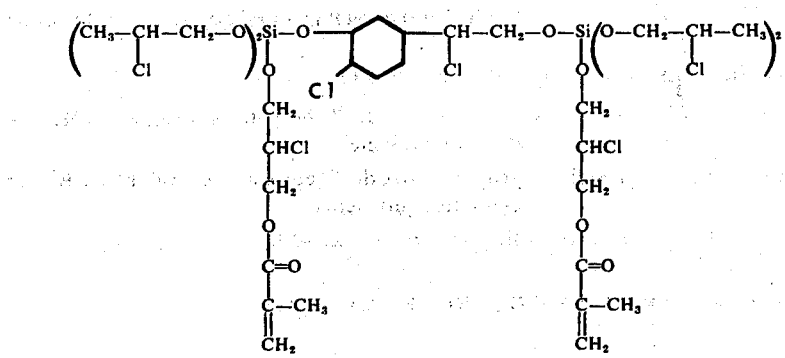
(62)

(SiCl₄ 1 mole; glycidyl methacrylate 1 epoxide equivalent; propylene oxide 2 epoxide equivalents; ERL 4206 1 epoxide equivalent)

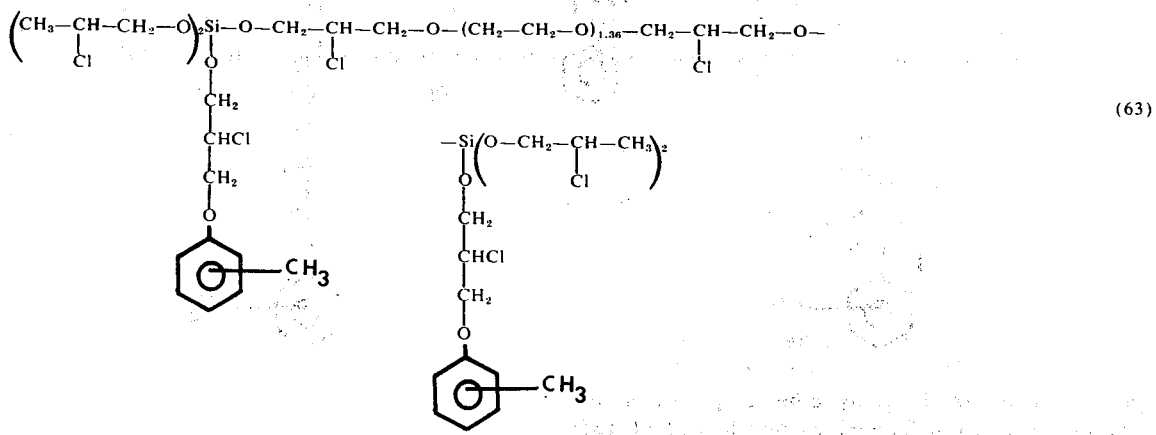

(63)

(SiCl₄ 1 mole; cresyl glycidyl ether 1 epoxide equivalent; propylene oxide 2 epoxide equivalents; DER 736 1 epoxide equivalent)

(SiCl₄ 1 mole; glycidyl methacrylate 2 epoxide equivalents; ethylene oxide 1 epoxide equivalent; RD 2 2 epoxide equivalent)

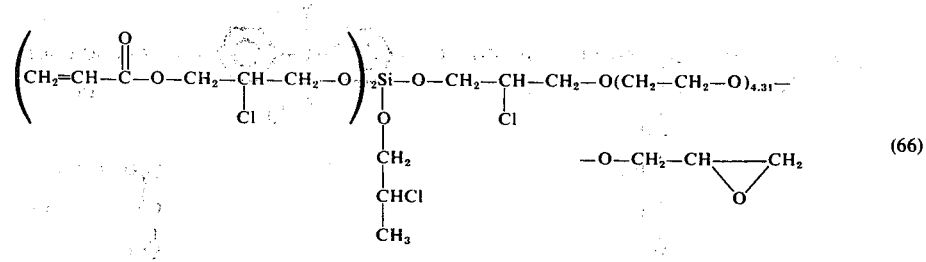

(66)

Where the amount of diepoxide used is 2 epoxide equivalents, the reaction product includes compounds containing a free epoxy group. These compounds can be represented by the formula (SiCl₄ 1 mole; glycidyl acrylate 2 epoxide equivalents; propylene oxide 1 epoxide equivalent; DER 732 2 epoxide equivalents)

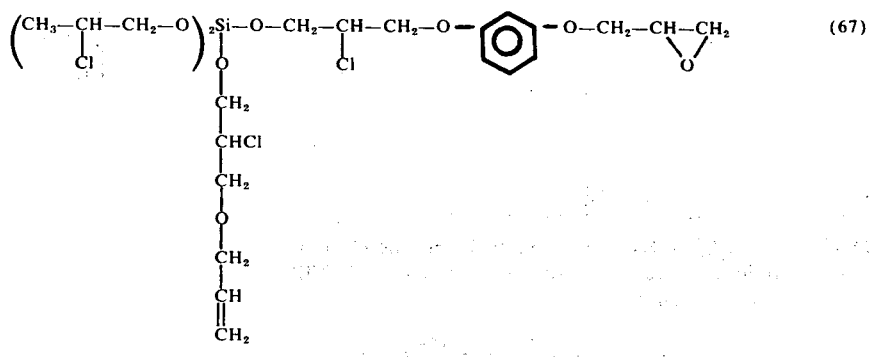

(67)

Illustrative of such compounds include the following:

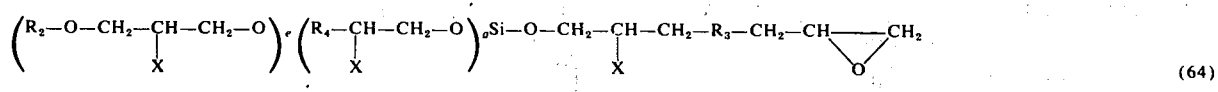

(64)

(SiCl₄ 1 mole; allyl glycidyl ether 1 epoxide equivalent; propylene oxide 2 epoxide equivalents; ERE 1359 2 epoxide equivalents)

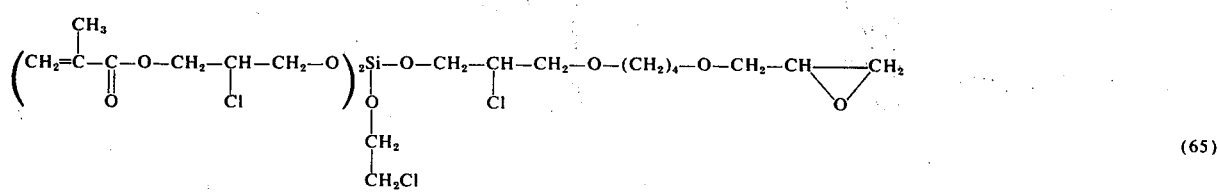

(65)

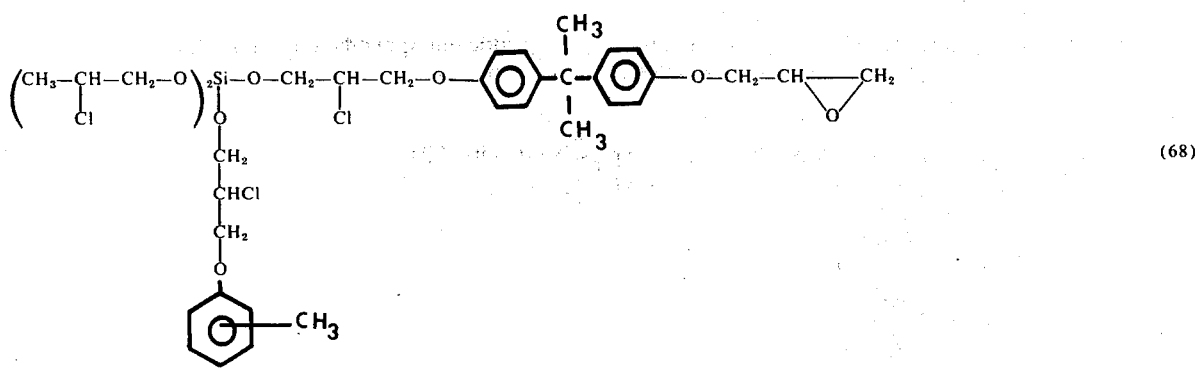
(68)
(SiCl₄ 1 mole; cresyl glycidyl ether 1 epoxide equivalent; propylene oxide 2 epoxide equivalents; DER 332 2 epoxide equivalents)
2 epoxide equivalents)
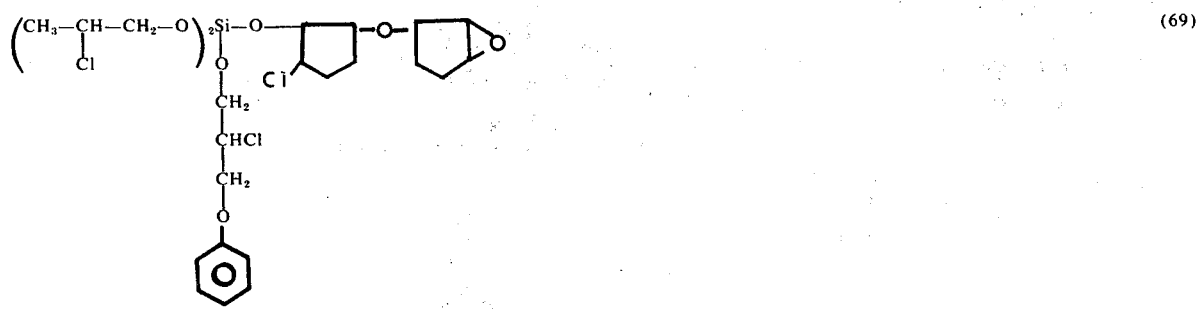
(69)
(SiCl₄ 1 mole, phenyl glycidyl ether 1 epoxide equivalent; propylene oxide 2 epoxide equivalents; ERL 4206
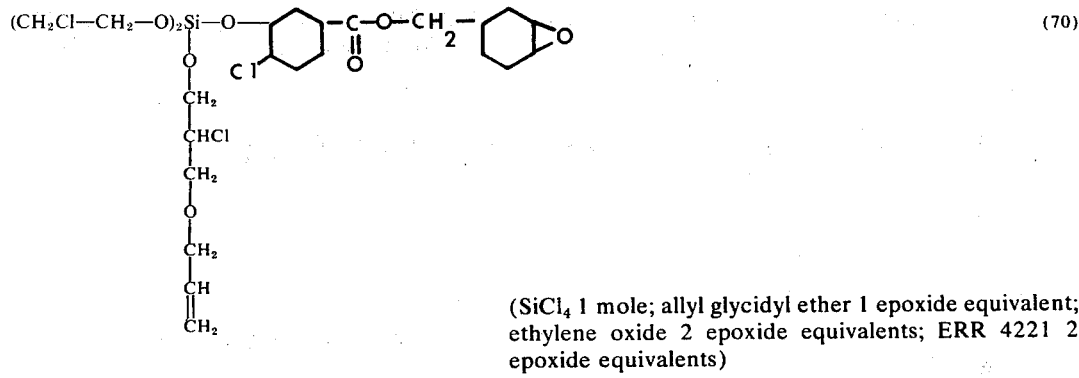
(70)
(SiCl₄ 1 mole; allyl glycidyl ether 1 epoxide equivalent; ethylene oxide 2 epoxide equivalents; ERR 4221 2 epoxide equivalents)
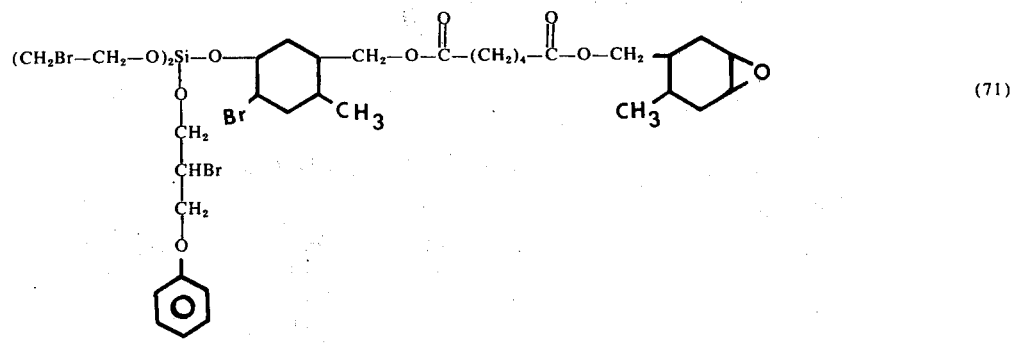
(71)

(SiBr₄ 1 mole; phenyl glycidyl ether 1 epoxide equivalent; ethylene oxide 2 epoxide equivalents; ERR 4289 2 epoxide equivalents)

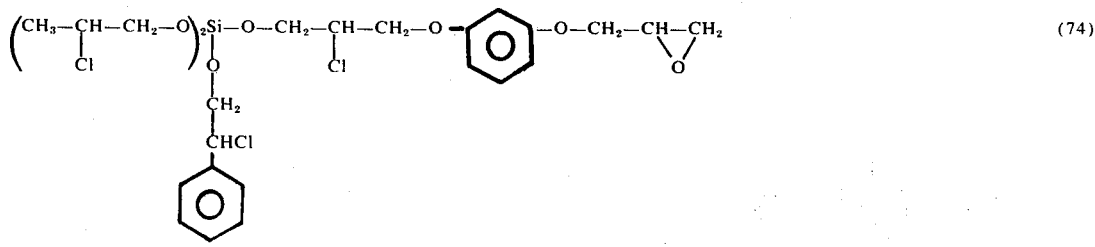

(74)

As will be appreciated by those skilled in the art, styrene oxide can be used in lieu of the monoepoxide containing the functional group as described above. The reaction product thus includes the following compounds:

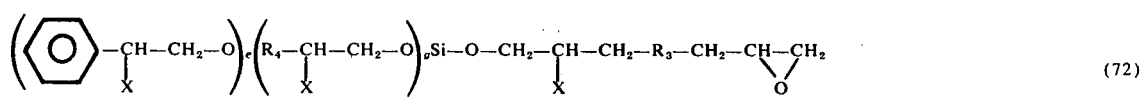

(72)

and

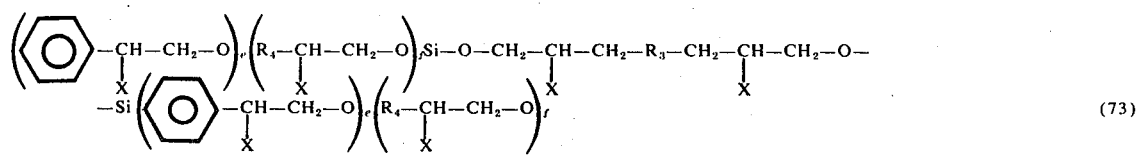

(73)

Specific compounds are illustrated by way of the following:

(SiCl₄ 1 mole; styrene oxide 1 epoxide equivalent; propylene oxide 2 epoxide equivalents; ERE 1359 2 epoxide equivalents)

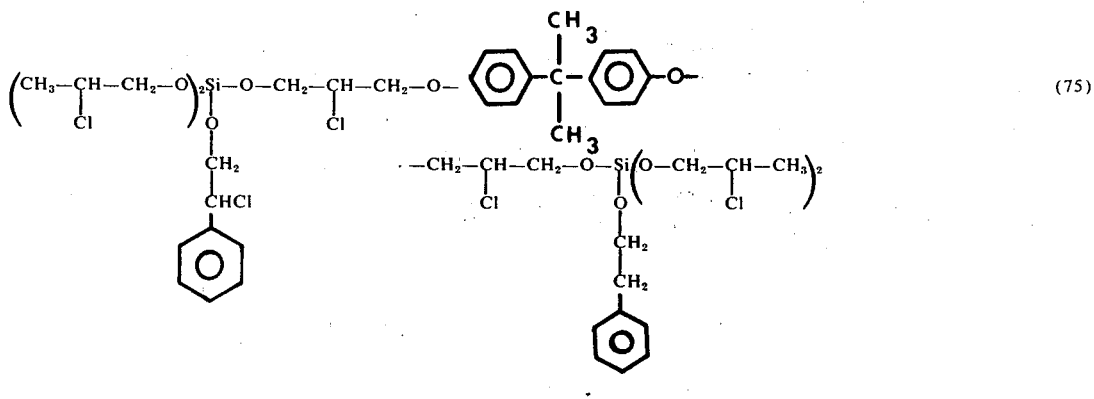

(75)

(SiCl₄ 1 mole; styrene oxide 1 epoxide equivalent; propylene oxide 2 epoxide equivalents; DER 332 1 epoxide equivalent)

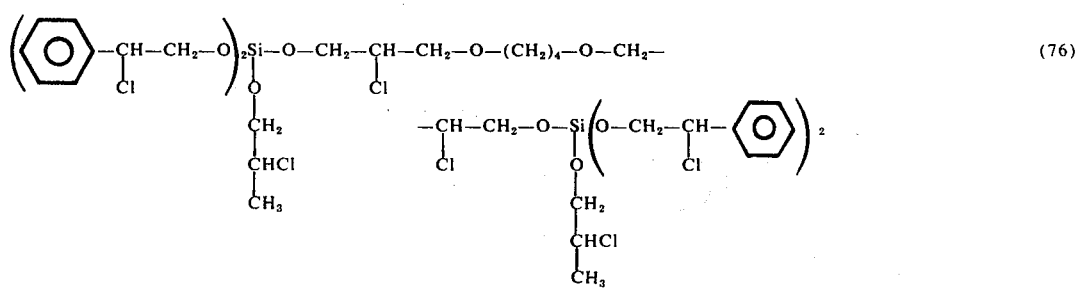

(76)

(SiCl$_4$ 1 mole; styrene oxide 2 epoxide equivalents; propylene oxide 1 epoxide equivalent; RD 2 1 epoxide equivalent)

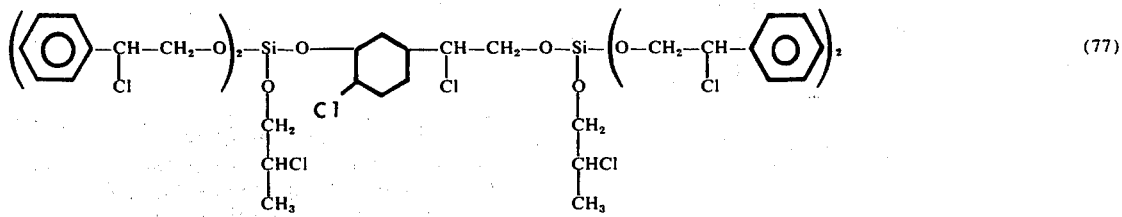
(77)

(SiCl$_4$ 1 mole; styrene oxide 2 epoxide equivalents; propylene oxide 1 epoxide equivalent; RD 4 1 epoxide equivalent)

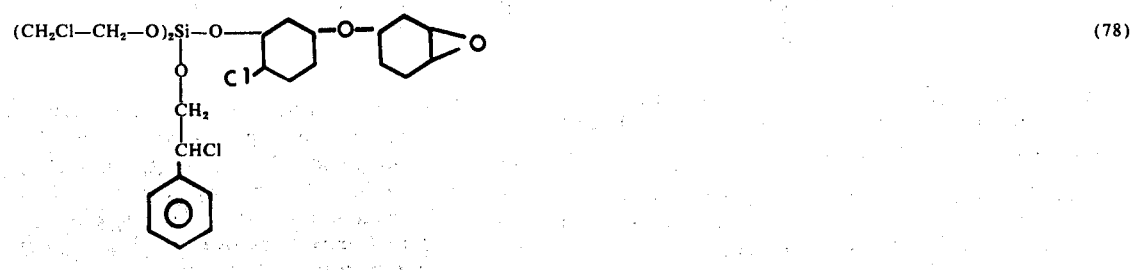
(78)

(SiCl$_4$ 1 mole; styrene oxide 1 epoxide equivalent; ethylene oxide 2 epoxide equivalents; ERR 4205 2 epoxide equivalents)

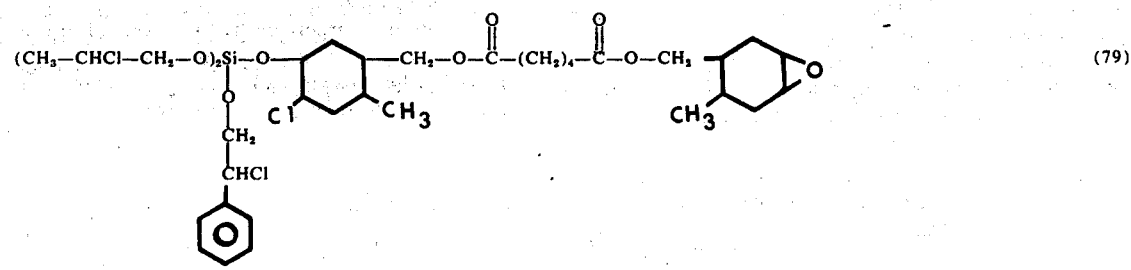
(79)

(SiCl$_4$ 1 mole; styrene oxide 1 epoxide equivalent; propylene oxide 2 epoxide equivalents; ERR 4289 2 epoxide equivalents)

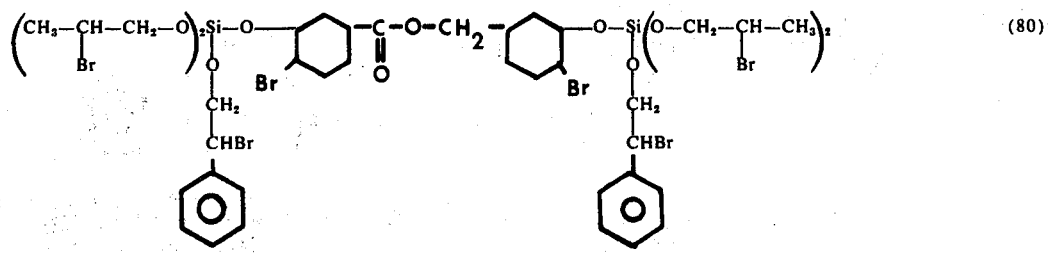
(80)

(SiBr$_4$ 1 mole; styrene oxide 1 epoxide equivalent; propylene oxide 2 epoxide equivalents; ERR 4221 1 epoxide equivalent)

In the practice of the above embodiment, it is generally desirable to react the diepoxide last, that is, after the alkylene oxide and the monoepoxide has been reacted with the halosilane. The monoepoxide and the alkylene oxide can be reacted with the silane in any order, or simultaneously, and the resulting product is preferably reacted with the diepoxide. It is generally preferred that the total of the number of epoxide equivalents of the monoepoxide and the alkylene oxide equal at least 2.1 to minimize polymer formation.

It is sometimes desirable that the products of this invention contain one or two oxy groups bonded directly to the silicon atom which does not have the increased resistance to hydrolysis which characterizes the Compounds which can be prepared in this manner have the general formula:

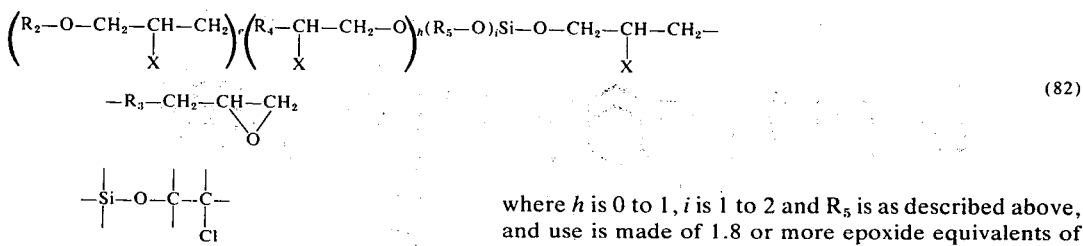

(82)

group. According to another embodiment of the invention, all or a portion of the alkylene oxide reactant can be replaced by an alcohol, and preferably a monohydric alcohol. For this purpose, use can be made of a compound having the formula $$R_5 - OH \qquad (81)$$

wherein $R_5$ is $C_1$ to $C_6$ alkyl (e.g., methyl, ethyl, propyl, etc.), benzyl, $C_2$ to $C_6$ alkenyl (e.g., vinyl, allyl, butenyl, etc.) or an aminoalkyl group containing 2 to 6 carbon atoms (e.g., aminoethyl, aminopropyl, aminobutyl, etc.).

Compounds which can be used in accordance with this embodiment of the invention include methanol, ethanol, propanol, isopropanol, benzyl alcohol, allyl alcohol and the alkanolamines, such as ethanolamine, propanolamine, butanolamine, etc.

As with the previous embodiments, the reaction product is a mixture of compounds which can be utilized as such or, if desired, compounds predominating where $h$ is 0 to 1, $i$ is 1 to 2 and $R_5$ is as described above, and use is made of 1.8 or more epoxide equivalents of the diepoxide. Where use is made of less than 2, both epoxide groups of the diepoxide generally react with the halosilane to form a reaction product which includes the following compounds:

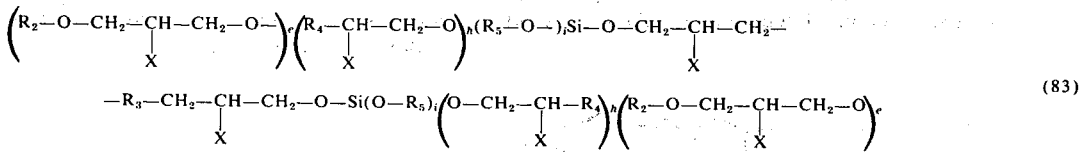

(83)

In the practice of this concept of the invention, use is made of from 0.5 to 2 epoxide equivalents of the functional monoepoxide, 0 to 1 epoxide equivalents of the alkylene oxide and 1 to 2 hydroxy equivalents of the alcohol. The amount of the diepoxide generally ranges from 0.5 to 2 epoxide equivalents. It is frequently preferred that the total of the functional monoepoxide, the alkylene oxide, if any, and the alcohol be at least 2.1 and preferably 2.5 to minimize polymer formation. It is also preferred that the diepoxide be reacted with halosilane after reaction with the other components of the reaction mixture.

As will be appreciated by those skilled in the art, the reaction product includes somewhat analogous compounds where use is made of styrene oxide in lieu of the functional monoepoxide as follows:

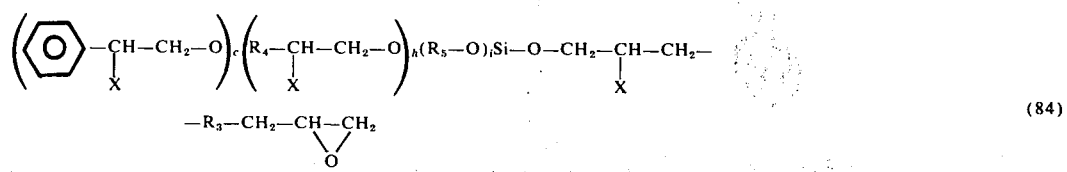

(84)

the reaction product can be isolated as described above.

and/or

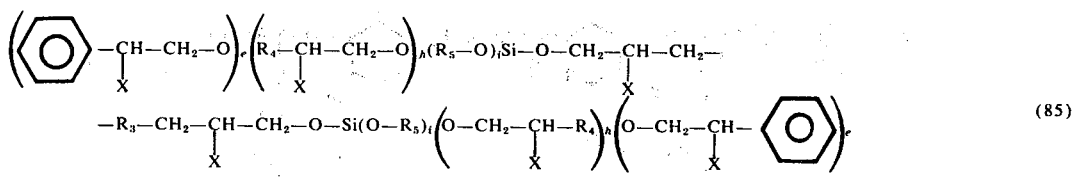

(85)

Compounds which can be prepared in accordance with this concept include the following:

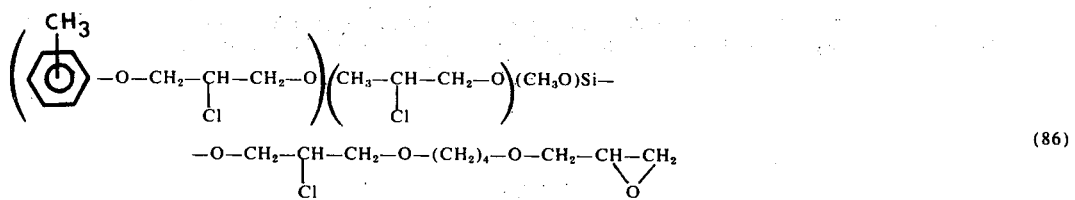

(86)

-continued (SiCl₄ 1 mole; cresyl glycidyl ether 1 epoxide equivalent; propylene oxide 1 epoxide equivalent; methanol 1 mole; RD 2 2 epoxide equivalents)

allyl alcohol 1 mole; DER 332 1 epoxide equivalent)

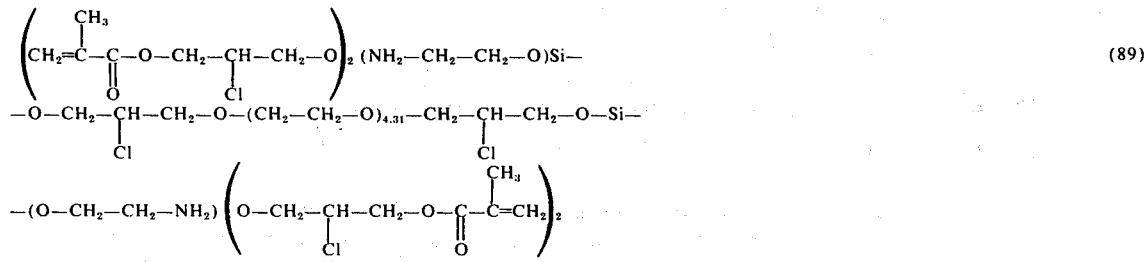
(89)

(SiCl₄ 1 mole; glycidyl methacrylate 2 epoxide equivalents; ethanol amine 1 mole; DER 732 1 epoxide equivalent)

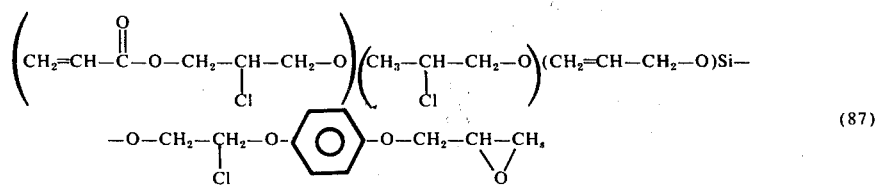
(87)

(SiCl₄ 1 mole; glycidyl acrylate 1 epoxide equivalent; propylene oxide 1 epoxide equivalent; allyl alcohol 1 mole; ERE 1359 2 epoxide equivalents)

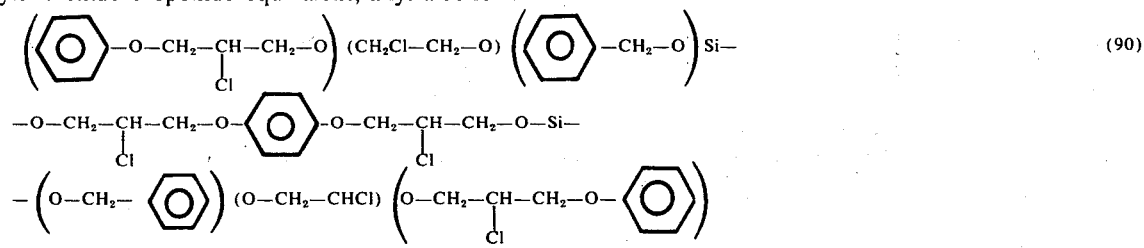
(90)

(SiCl₄ 1 mole; phenyl glycidyl ether 1 epoxide equivalent; benzyl alcohol 1 mole; ERE 1359 1 epoxide equivalent; 1 ethylene oxide epoxide equivalent)

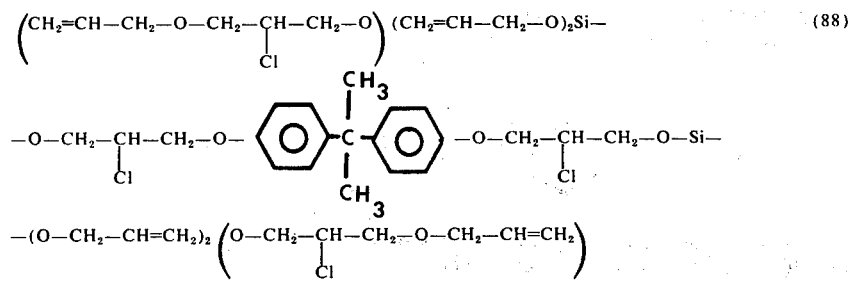
(88)

(SiCl₄ 1 mole; allyl glycidyl ether 1 epoxide equivalent;

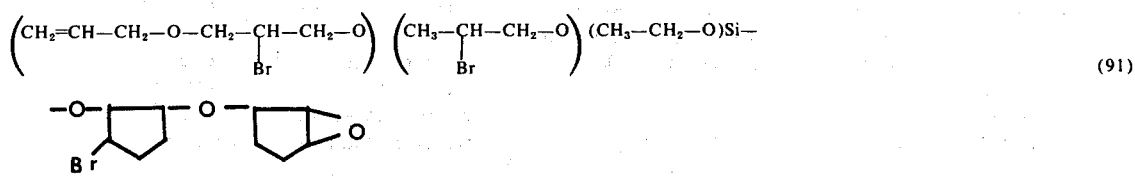
(91)

(SiBr₄ 1 mole; allyl glycidyl ether 1 epoxide equivalent; propylene oxide 1 epoxide equivalent; ethanol 1 mole; ERR 4205 2 epoxide equivalents)

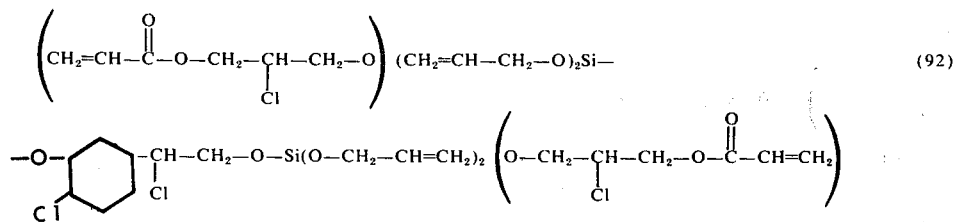

(SiCl₄ 1 mole; glycidyl methacrylate 1 epoxide equivalent; allyl alcohol 2 mole; RD 4 1 epoxide equivalent)

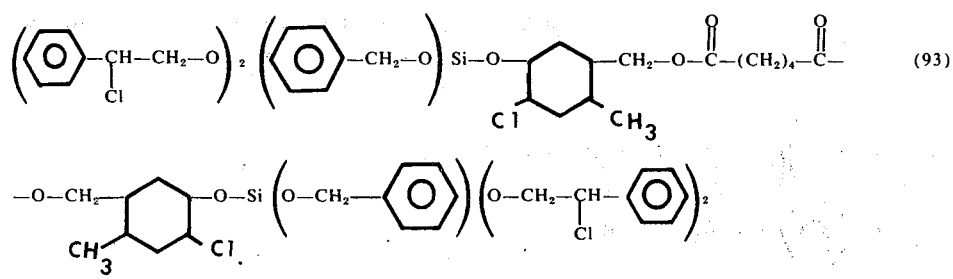

(SiCl₄ 1 mole; styrene oxide 2 epoxide equivalents; benzyl alcohol 1 mole; ERL 4289 1 epoxide equivalent)

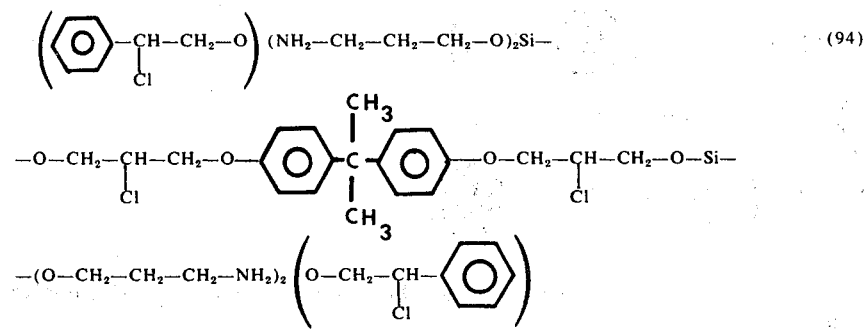

(SiCl₄ 1 mole; styrene oxide 1 epoxide equivalent; propanol amine 2 mole; DER 332 1 epoxide equivalent)

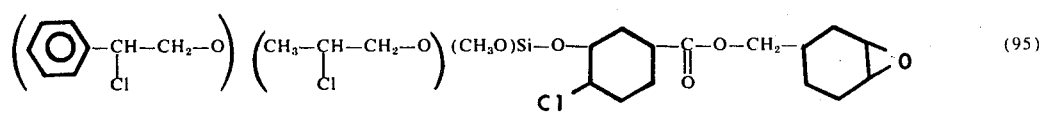

(SiCl₄ 1 mole; styrene oxide 1 epoxide equivalent; propylene oxide 1 epoxide equivalent; methanol 1 mole; ERR 4221 2 epoxide equivalents).

In accordance with yet another embodiment of the invention, the halosilane employed in the reaction can contain one or more organo groups attached directly to the silicon atom through a carbon-to-silicon bond. In the preferred practice of this embodiment, the halosilane is of the formula $$(R_6)_n SiX_{(4-n)} \qquad (96)$$

wherein $R_6$ is an organic group containing 1 to 20 carbon atoms, $n$ is an integer from 1 to 2 and X is halogen and preferably chlorine or bromine.

$R_6$ is preferably alkyl containing 1 to 20, and preferably 1 to 6, carbon atoms (e.g., methyl, ethyl, propyl, isopropyl, lauryl, etc.); alkenyl containing 2 to 20, and preferably 2 to 6, carbon atoms (e.g., vinyl, allyl, 3-butenyl, 4-pentenyl, etc.), cycloalkyl, such as cyclopentyl, cyclohexyl, etc., phenyl, as well as substituted derivatives thereof.

Where the organo halosilanes described above are reacted with a monoepoxide and at least one diepoxide as described above, it is preferred to employ from 0.5 to 2.0 epoxide equivalents of the diepoxide and from 1 to 3 epoxide equivalents of the monoepoxide. The reaction mixtures can optionally include 1 to 2 moles of an alkylene oxide and/or an alcohol as described above.

As is the case in the embodiments described above the reaction product is generally in the form of a mixture of compounds. Compounds which can be separated from the resulting product include the following

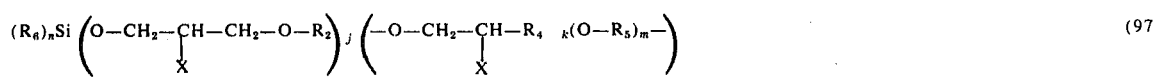

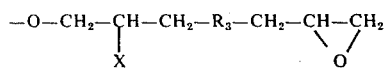

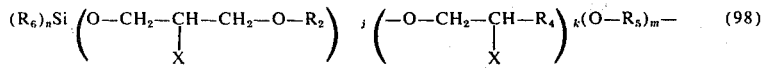
(98)

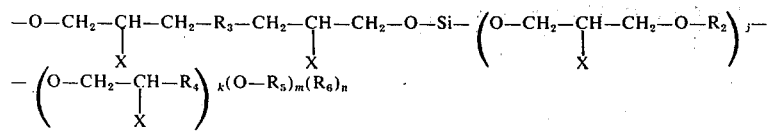

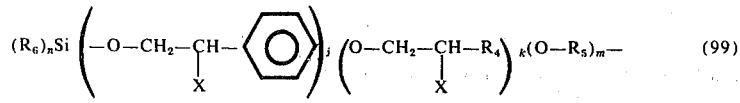
(99)

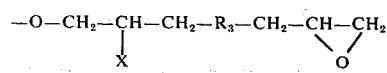

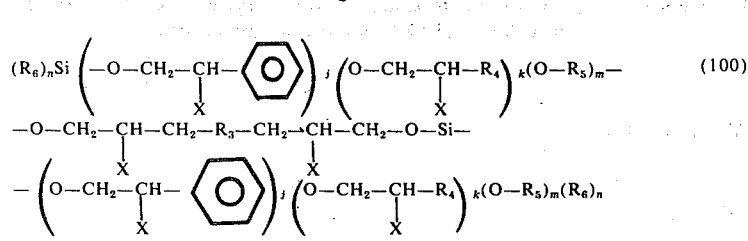
(100)

wherein $j$ is an integer from 1 to 2 when $n = 1$, and $j$ is 1 when $n = 2$; where $k$ is 0 or 1 and $m$ is 0 or 1, provided that $k + m = 1$.

Specific examples of such compounds include the following:

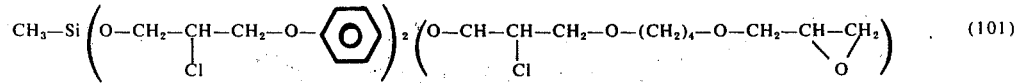
(101)

($CH_3SiCl_3$ 1 mole; phenyl glycidyl ether 2 epoxide equivalents; RD 2 2 epoxide equivalents)

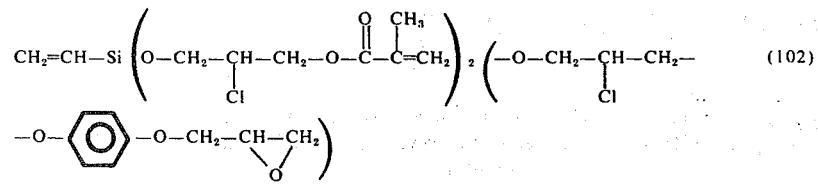
(102)

($CH_2CHSiCl_3$ 1 mole; glycidyl methacrylate 2 epoxide equivalents; ERE 1359 2 epoxide equivalents)

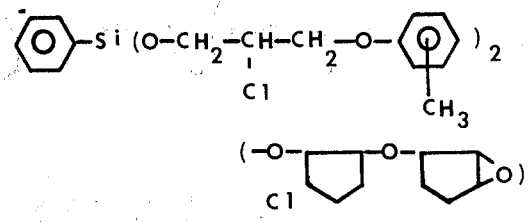

(Phenyltrichlorosilane 1 mole; cresyl glycidyl ether 2 epoxide equivalents; ERR 4205 2 epoxide equivalents)

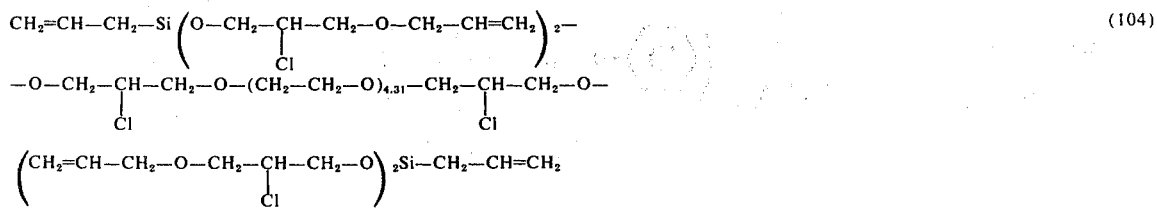
(104)

(Allyl trichlorosilane 1 mole; allyl glycidyl ether 2 epoxide equivalents, DER 732 1 epoxide equivalent)

(Ethyltrichlorosilane 1 mole; methyl glycidyl ether 1 epoxide equivalent; methanol 1 mole; DER 332 1 epoxide equivalent)

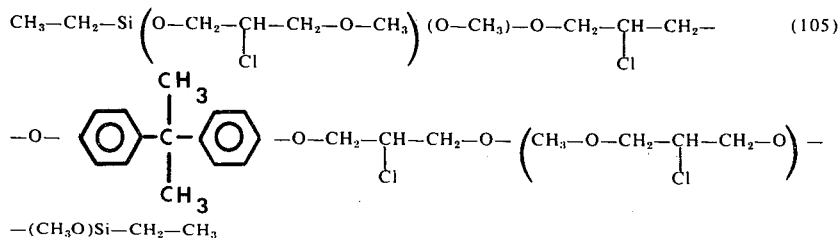  (105)

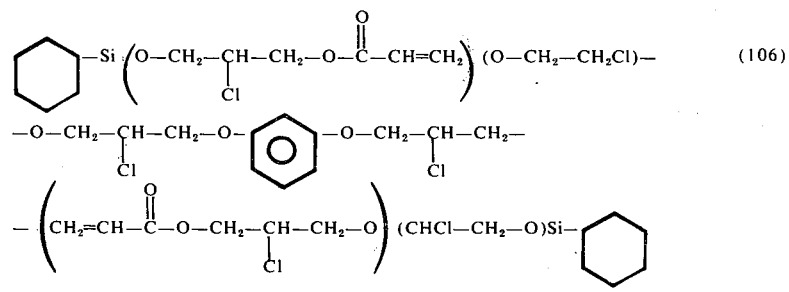  (106)

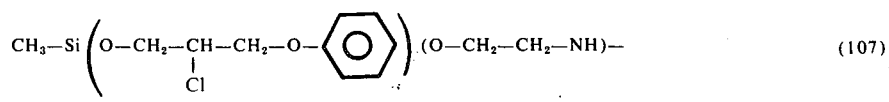  (107)

(Methyltrichlorosilane 1 mole; phenyl glycidyl ether 1 epoxide equivalent; ethanol amine 1 mole; ERR 4221 1 mole)

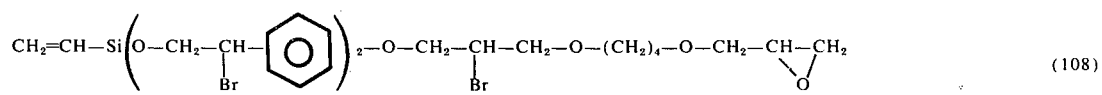  (108)

(Vinyl tribromosilane 1 mole; styrene oxide 1 epoxide equivalent; RD 2 2 epoxide equivalents)

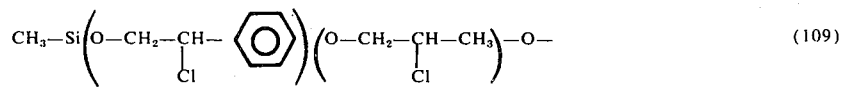  (109)

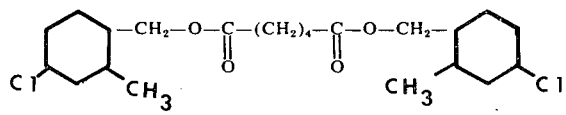

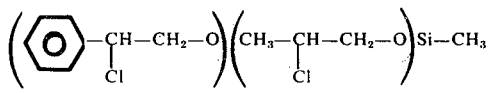

(Cyclohexyltrichlorosilane 1 mole; glycidyl acrylate 1 epoxide equivalent; ethylene oxide 1 mole; ERE 1359 1 epoxide equivalent)

(Methyltrichlorosilane 1 mole; styrene oxide 1 epoxide equivalent; propylene oxide 1 mole; ERR 4289 1 epoxide equivalent).

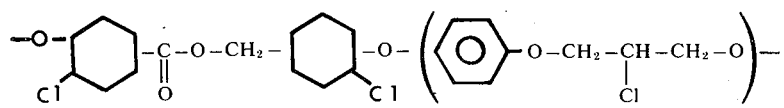

The compounds and mixtures of compounds produced in accordance with the concepts of this invention can be used in a wide variety of applications in which the organosilicon compounds described in formula (1) above have been used. It has been found that the organosilicon compounds of this invention are effective in the treatment of glass fibers to improve the bonding relationship between glass fibers and resinous plastics and elastomeric materials. For example, the compounds of this invention or the mixtures of compounds produced in accordance with this invention can be applied as a thin coating to individual glass fiber filaments and the coated glass fiber filaments can then be employed as reinforcement for resins and elastomeric materials. Alternatively, the compounds and mixtures of compounds prepared in accordance with this invention can be formulated into impregnating compositions for use in the impregnation of bundles of glass fibers for reinforcement of elastomeric materials as in the manufacture of glass fiber reinforced elastomeric products including rubber tires, drive belts, timing belts, etc.

Having described the basic concepts of the present invention, reference is now made to the following examples which are provided by way of illustration, and not by way of limitation, of the practice of this invention.

EXAMPLE 1

Into a round bottom flask equipped with a stir rod, a thermometer and a reflux condenser, there is introduced 1 mole of silicon tetrachloride. Thereafter, 3 epoxide equivalents of phenyl glycidyl ether are slowly added to the reaction vessel and the reaction commences with the evolution of heat. After addition of the phenyl glycidyl ether, 1 mole (2 epoxide equivalents) of the diepoxide RD 2 is added to the flask. The resulting mixture is then allowed to stand for one hour at room temperature.

Analysis of the reaction product reveals the presence of a mixture of compounds. From this mixture there is separated the organosilicon compound identified as (22) above.

EXAMPLE 2

Using the procedure described in Example 1, 1 mole of silicon tetrachloride is reacted with 3 epoxide equivalents of allyl glycidyl ether and 2 epoxide equivalents of the diepoxide DER 332.

Analysis of the reaction mixture reveals that the reaction mixture is composed of several different compounds. One of the compounds which can be separated from the reaction mixture is compound (23).

EXAMPLE 3

Using the procedure described in Example 1, 1 mole of silicon tetrachloride is reacted with 3 epoxide equivalents of glycidyl acrylate and 2 epoxide equivalents of the diepoxide ERE 1359. The reaction product is found to include mixtures of compounds including the compound (24) containing a free epoxide group.

EXAMPLE 4

One mole of silicon tetrabromide is reacted with 3 epoxide equivalents of aminophenyl glycidyl ether and 2 epoxide equivalents of the diepoxide DER 332. A mixture of compounds is found in the reaction product.

EXAMPLE 5

Using the procedure described in Example 1, 1 mole of silicon tetrachloride is reacted with 3 epoxide equivalents of allyl glycidyl ether and 2 epoxide equivalents of the cyclohexane diepoxide RD 4. The reaction mixture is subjected to analysis and is found to contain the compound (26) as well as the compound in which the silicon atom is bonded through an oxygen atom to the cyclohexane ring.

EXAMPLE 6

Using the procedure described in Example 1, 1 mole of silicon tetrachloride is reacted with 3 epoxide equivalents of glycidyl acrylate and 1 epoxide equivalent of the diepoxide RD 2. The resulting reaction mixture is found to contain a mixture of compounds from which can be separated the compound (30).

EXAMPLE 7

One mole of silicon tetrachloride is reacted with cresyl glycidyl ether (3 epoxide equivalents) and 1 epoxide equivalent of the diepoxide ERE 1359. The reaction mixture is subjected to analysis and is found to contain compound (31) which can be separated therefrom by liquid chromatography.

EXAMPLE 8

One mole of silicon tetrachloride is reacted with 3 epoxide equivalents of allyl glycidyl ether and 1 epoxide equivalent of the diepoxide DER 332. The reaction mixture is found to contain compound (32) which can be separated therefrom in admixture with other reaction products.

EXAMPLE 9

Using the procedure described in Example 1, 1 mole of silicon tetrachloride is reacted with 3 epoxide equivalents of Epoxide No. 7 from Procter and Gamble and 1 epoxide equivalent of the diepoxide DER 332. The reaction mixture is found to contain a mixture of compounds which can be utilized as such or, if desired, individual compounds contained therein can be subjected to purification.

EXAMPLE 10

One mole of silicon tetrachloride is reacted with 3 epoxide equivalents of phenyl glycidyl ether and 1 epoxide equivalent of the cyclohexane diepoxide ERR 4221. The resulting mixture is subjected to analysis and found to contain the compound (34) which can be separated therefrom by liquid chromatography.

EXAMPLE 11

One mole of silicon tetrachloride is reacted with 3 epoxide equivalents of allyl glycidyl ether and 1 epoxide equivalent of the cyclohexane diepoxide ERR 4289. The reaction mixture is then subjected to purification to isolate the compound (36).

EXAMPLE 12

One mole of silicon tetrachloride is reacted with 2 epoxide equivalents of glycidyl methacrylate and 1 epoxide equivalent of allyl glycidyl ether. The resulting mixture is then reacted with 1 epoxide equivalent of the diepoxide DER 332. The resulting product is subjected to analysis and is found to contain a mixture of complex organosilicon compounds.

EXAMPLE 13

One mole of silicon tetrachloride is reacted with 2 epoxide equivalents of glycidyl methacrylate and 1 epoxide equivalent of Epoxide No. 8 from Procter and Gamble. The resulting product is then reacted with the diepoxide ERE 1359 to produce a mixture of complex organosilicon compounds.

EXAMPLE 14

Using the procedure described in Example 1, 1 mole of silicon tetrachloride is reacted with 3 epoxide equivalents of styrene oxide and 1 epoxide equivalent of the diepoxide ERE 1359. The resulting product is subjected to analysis and found to contain a mixture of compounds including compound (42) which can be separated from the reaction mixture by liquid chromatography.

EXAMPLE 15

One mole of silicon tetrachloride is reacted with 3 epoxide equivalents of styrene oxide and 1 epoxide equivalent of the cyclohexane diepoxide ERR 4205. The resulting product is subjected to analysis and found to contain compound (44) which can be separated from the reaction mixture in a conventional manner.

EXAMPLE 16

Using the procedure described in Example 1, 1 mole of silicon tetrachloride is reacted with 1 epoxide equivalent of propylene oxide and 2 epoxide equivalents of allyl glycidyl ether. The resulting product is then reacted with 1 epoxide equivalent of the diepoxide RD 2.

The resulting reaction mixture is subjected to analysis and is found to contain a mixture of compounds including the compound (48) which can be separated therefrom by liquid chromatography.

EXAMPLE 17

Using the procedure of Example 16, 1 mole of silicon tetrachloride is reacted with 2 epoxide equivalents of propylene oxide and 1 epoxide equivalent of allyl glycidyl ether. The resulting product is then reacted with 0.5 epoxide equivalents of the diepoxide DER 332 and 0.5 epoxide equivalents of the diepoxide DER 736. The resulting product is found to contain a mixture of complex organosilicon compounds.

EXAMPLE 18

One mole of silicon tetrachloride is reacted with 2 epoxide equivalents of propylene oxide and 1 epoxide equivalent of allyl glycidyl ether. The product is then reacted with 0.5 epoxide equivalents of the diepoxide DER 332 and 0.5 epoxide equivalents of the diepoxide ERR 4205.

EXAMPLE 19

One mole of silicon tetrachloride is reacted with 2 epoxide equivalents of propylene oxide and 0.5 epoxide equivalents of allyl glycidyl ether. The resulting product is then reacted with 0.5 epoxide equivalents of each of the diepoxides ERE 1359, DER 736 and ERL 4206.

EXAMPLE 20

One mole of silicon tetrachloride is reacted with 2.5 epoxide equivalents of propylene oxide and 0.5 epoxide equivalents of Epoxide No. 7 from Procter and Gamble. The product of this reaction is then reacted with 1 epoxide equivalent of the diepoxide ERE 1359.

The resulting product is a mixture of complex organosilicon compounds.

EXAMPLE 21

One mole of silicon tetrachloride is reacted with 1 epoxide equivalent of glycidyl acrylate and 2 epoxide equivalents of propylene oxide. The resulting product is then reacted with 1 epoxide equivalent of the diepoxide ERE 1359.

The product is found to contain a mixture of compounds, including compound (51) which can be separated therefrom by conventional techniques.

EXAMPLE 22

One mole of silicon tetrachloride is reacted with 1 epoxide equivalent of allyl glycidyl ether and 2 epoxide equivalents of propylene oxide. Thereafter, 1 epoxide equivalent of the diepoxide ERR 4289 is added to the reaction vessel to produce a mixture of compounds including compound (54) which can be separated from the reaction mixture, if desired.

EXAMPLE 23

One mole of silicon tetrachloride is reacted with 2 epoxide equivalents of propylene oxide and 1 epoxide equivalent of allyl glycidyl ether. The product is then reacted with the diepoxide DER 332 (1 epoxide equivalent) to produce a mixture of compounds. Compound (56) can be separated therefrom by conventional techniques.

EXAMPLE 24

One mole of silicon tetrachloride is reacted with 2 epoxide equivalents of propylene oxide and 1 epoxide equivalent of allyl glycidyl ether. The product is then reacted with the cyclohexane diepoxide ERL 4206 (1 epoxide equivalent) to produce a reaction mixture containing compound (57).

EXAMPLE 25

Using the procedure as described above, 1 mole of silicon tetrachloride is reacted with 1 epoxide equivalent of allyl glycidyl ether and 2 epoxide equivalents of propylene oxide. Thereafter, there is added to the reaction mixture 1 epoxide equivalent of the diepoxide ERE 1359. The product, which is a mixture of compounds, is found to include compound (59) which can be separated therefrom if desired.

EXAMPLE 26

One mole of silicon tetrachloride is reacted with 2 epoxide equivalents of propylene oxide and 1 epoxide equivalent of glycidyl methacrylate. The diepoxide DER 332 (1 epoxide equivalent) is then added to the reaction mixture to form a mixture of complex organosilicon compounds including the compound (61) which can be separated from the reaction mixture by liquid chromatography, if desired.

EXAMPLE 27

One mole of silicon tetrachloride is reacted with 2 epoxide equivalents of propylene oxide and 1 epoxide equivalent of cresyl glycidyl ether. The product of this reaction is then reacted with 1 epoxide equivalent of the diepoxide DER 736 to form a mixture of compounds including compound (63).

EXAMPLE 28

One mole of silicon tetrachloride is reacted with 2 epoxide equivalents of propylene oxide and 1 epoxide equivalent of allyl glycidyl ether. Thereafter, 2 epoxide equivalents of the diepoxide ERE 1359 are added to the reaction mixture to form a mixture of compounds including the compound (67) containing a free epoxy group. Compound (67) can be separated from the reaction mixture, if desired, by liquid chromatography.

EXAMPLE 29

One mole of silicon tetrachloride is reacted with 2 epoxide equivalents of propylene oxide and 1 epoxide equivalent of cresyl glycidyl ether. Thereafter, 2 epoxide equivalents of DER 332 are added. The resulting product is found to contain compound (68).

EXAMPLE 30

One mole of silicon tetrachloride is reacted with 2 epoxide equivalents of propylene oxide and 1 epoxide equivalent of phenyl glycidyl ether. Thereafter, the resulting product is reacted with cyclohexane diepoxide ERL 4206 (2 epoxide equivalents) to form a reaction mixture containing compound (69) which can be separated therefrom by conventional techniques, if desired.

EXAMPLE 31

One mole of silicon tetrachloride is reacted with 2 epoxide equivalents of propylene oxide and 1 epoxide equivalent of styrene oxide. The product of this reaction is then reacted with two epoxide equivalents of the diepoxide ERE 1359 to form the compound (74) in addition to other complex reaction products. Compound (74) can be separated from the reaction mixture, if desired.

EXAMPLE 32

One mole of silicon tetrabromide is reacted with 2 epoxide equivalents of propylene oxide and 1 epoxide equivalent of styrene oxide. Thereafter, 1 epoxide equivalent of the cyclohexane diepoxide ERR 4221 is added to form a mixture of compounds including compound (80) which can be separated therefrom by conventional techniques.

EXAMPLE 33

One mole of silicon tetrachloride is reacted with 1 epoxide equivalent of propylene oxide, 1 epoxide equivalent of cresyl glycidyl ether and 1 mole of methanol. The resulting product is then reacted with 2 epoxide equivalents of the diepoxide RD 2 to form a mixture of complex organosilicon compounds including compound (86) which is separated from the reaction mixture by liquid chromatography.

EXAMPLE 34

Using the procedures described in the previous Examples, 1 mole of silicon tetrachloride is reacted with 2 epoxide equivalents of glycidyl methacrylate and 1 mole of ethanol amine. The product of this reaction is then reacted with 1 epoxide equivalent of the diepoxide DER 732 to form a mixture of compounds including compound (89) which can be separated from the reaction mixture, if desired.

EXAMPLE 35

Using the procedure described above, 1 mole of silicon tetrachloride is reacted with 2 epoxide equivalents of styrene oxide and 1 mole of benzyl alcohol. The product of this reaction is then reacted with the diepoxide ERR 4289 to form a mixture of complex organosilicon compounds including the compound (93).

EXAMPLE 36

One mole of vinyl trichlorosilane is reacted with 2 epoxide equivalents of glycidyl methacrylate and then with 2 epoxide equivalents of the diepoxide ERE 1359. The resulting product is a mixture of compounds including compound (102) which can be separated from the reaction mixture, if desired, by liquid chromatography.

EXAMPLE 37

One mole of allyl trichlorosilane is reacted with 2 epoxide equivalents of allyl glycidyl ether and 1 epoxide equivalent of the diepoxide DER 732. The resulting product is a mixture of compounds including compound (104) which can be separated from the reaction mixture by conventional techniques.

It will be apparent from the foregoing that numerous changes and modifications can be made in the details of procedure, formulation and use without departing from the spirit of the invention, especially as defined in the following claims.

We claim:

1. Organo silicon compounds prepared by reaction of a halosilane selected from the group consisting of an organo halosilane having the formula $(R_6)_n SiX_{(4-n)}$ wherein $R_6$ is an organic group selected from the group consisting of alkyl, alkenyl, cycloalkyl and phenyl, n is an integer from 1 to 2 and X is halogen and a tetrahalosilane, with a monoepoxide selected from the group consisting of a styrene oxide and an epoxide having the formula

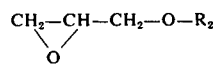

wherein $R_2$ is an organic group selected from the group consisting of phenyl and amino, halo and alkyl substituted phenyl, alkyl, alkenyl and a group having the formula

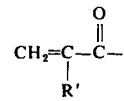

wherein R' is hydrogen or methyl, and at least one diepoxide selected from the group consisting of an epoxide of the formula

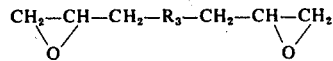

wherein $R_3$ is a divalent organic group selected from the group consisting of alkylene, alkyleneoxyalkylene, oxyalkyleneoxy, oxyalkyleneoxyalkyleneoxy, a group of the formula

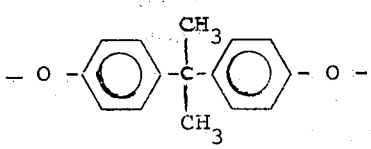

and a group of the formula

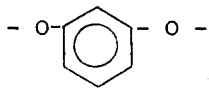

and a cyclohexane diepoxide, with the diepoxide being reacted in an amount less than two epoxide equivalents based upon a mole of silane.

2. Compounds as defined in claim 1 wherein the reaction mixture also includes a compound selected from the group consisting of an alkylene oxide, a monohydric alcohol and mixtures thereof.

3. Compounds as defined in claim 1 wherein the monoepoxide is reacted in an amount corresponding to 1 to 3 epoxide equivalents per mole of the halosilane and the diepoxide is reacted in an amount corresponding to 0.5 to 2 epoxide equivalents per mole of the halosilane.

4. Compounds as defined in claim 1 wherein the monoepoxide is reacted in an amount corresponding to at least 2.1 epoxide equivalents per mole of the halosilane.

5. Compounds as defined in claim 1 wherein the halosilane is a tetrahalosilane and the reaction mixture includes from 1 to 2 moles of an alkylene oxide and/or a monohydric alcohol per mole of the halosilane.

6. Organo silicon compounds prepared by reaction of a tetrahalosilane with a monoepoxide selected from the group consisting of a styrene oxide and an epoxide of the formula

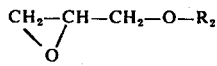

where $R_2$ is an organic group selected from the group consisting of phenyl and amino, halo and alkyl substituted phenyl, alkyl, alkenyl and a group having the formula

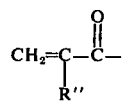

wherein R' is hydrogen or methyl and at least one diepoxide selected from the group consisting of an epoxide of the formula

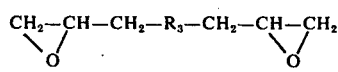

wherein $R_3$ is a divalent organic group selected from the group consisting of alkylene, alkyleneoxyalkylene, oxyalkyleneoxy, oxyalkyleneoxyalkyleneoxy, a group of the formula

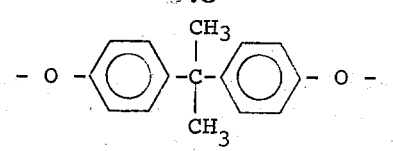

and a group of the formula

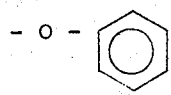

and a cyclohexane diepoxide, with the diepoxide being reacted in an amount less than two epoxide equivalents based upon a mole of silane.

7. Compounds as defined in claim 6 wherein the monoepoxide is present in an amount of at least 2.1 epoxide equivalents per mole of the tetrahalosilane.

8. Compounds as defined in claim 6 wherein the diepoxide is present in an amount of 0.5 to 2 epoxide equivalents per mole of the tetrahalosilane.

9. Compounds as defined in claim 6 wherein the reaction product includes at least one compound selected from the group consisting of compounds of the formula

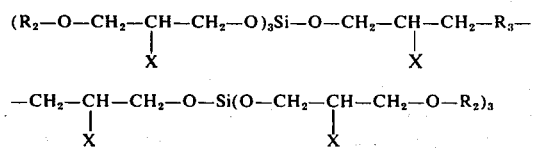

and compounds of the formula

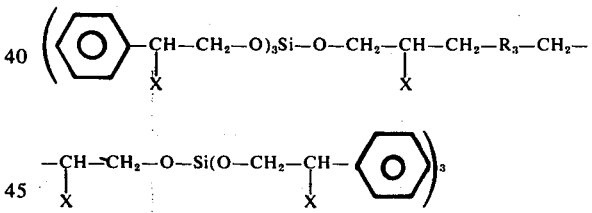

wherein X is halogen.

10. A compound selected from the group consisting of a compound of the formula

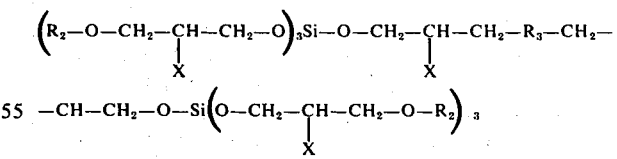

and a compound of the formula

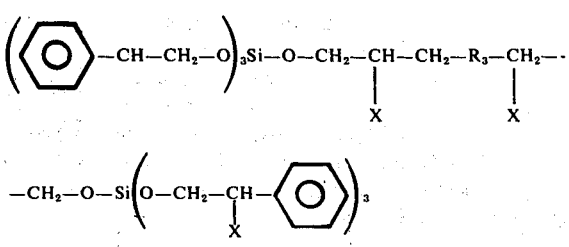

wherein $R_2$ is an organic group selected from the group consisting of phenyl and amino, halo and alkyl substituted phenyl, alkyl, alkenyl and a group having the formula

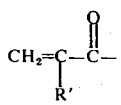

wherein R' is hydrogen or methyl, X is halogen and $R_3$ is a divalent organic group selected from the group consisting of alkylene, alkyleneoxyalkylene, oxyalkyleneoxy, oxyalkyleneoxyalkyleneoxy, a group of the formula

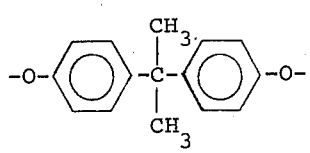

and a group of the formula

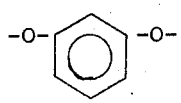

11. Organo silicon compounds prepared by reaction of a tetrahalosilane with (1) a monoepoxide selected from the group consisting of a styrene oxide and an epoxide of the formula

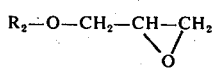

wherein $R_2$ is an organic group selected from the group consisting of phenyl and amino, halo and alkyl substituted phenyl, alkyl, alkenyl and a group having the formula

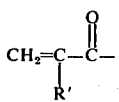

wherein R' is hydrogen or methyl, (2) at least one diepoxide selected from the group consisting of an epoxide of the formula

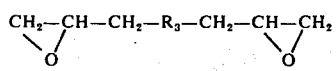

wherein $R_3$ is selected from the group consisting of alkylene, alkyleneoxyalkylene, oxyalkyleneoxy, oxyalkyleneoxyalkyleneoxy, a group of the formula

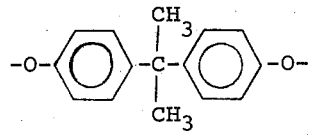

and a group of the formula

and a cyclohexane diepoxide, and (3) a compound selected from the group consisting of an alkylene oxide, a monohydric alcohol having the formula $R_5$-OH wherein $R_5$ is alkyl, aminoalkyl, benzyl and alkenyl, and mixtures thereof, with the diepoxide being reacted in an amount less than two epoxide equivalents based upon a mole of silane.

12. Organo silicon compounds as defined in claim 11 wherein the reaction mixture includes 0.5 to 2 epoxide equivalents of the monoepoxide, 0.5 to 2 epoxide equivalents of the diepoxide and 1 to 2 moles of said compound per mole of tetrahalosilane.

13. Organo silicon compounds as defined in claim 11 wherein the total of the epoxide equivalents of the monoepoxide and the moles of said compound is at least 2.1.

14. A compound selected from the group consisting of a compound of the formula

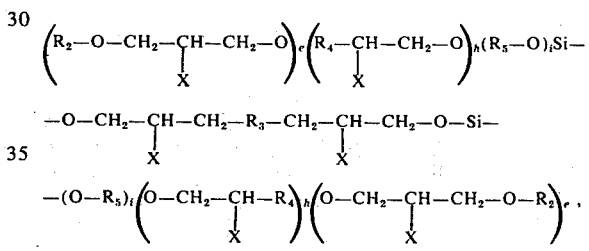

a compound of the formula

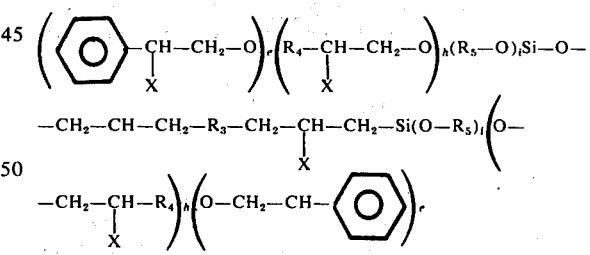

and mixtures thereof, wherein $R_2$ is an organic group selected from the group consisting of phenyl and amino, halo and alkyl substituted phenyl, alkyl, alkenyl and a group having the formula

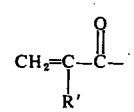

wherein R' is hydrogen or methyl, X is halogen, $R_4$ is hydrogen or alkyl, $R_5$ is selected from the group consisting of alkyl, alkenyl, benzyl and aminoalkyl, $R_3$ is a divalent organic group selected from the group consisting of alkylene, alkyleneoxyalkylene, oxyalkyleneoxy, oxyalkyleneoxyalkyleneoxy, a group of the formula

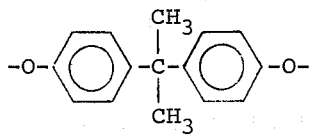

and a group of the formula

$h$ is an integer from 0 to 1, $i$ is an integer from 1 to 2 and $e$ is an integer from 1 to 2.

15. Organo silicon compounds prepared by reaction of (1) a halosilane having the formula
$$(R_6)_n SiX_{(4-n)}$$
wherein $R_6$ is an organic group selected from the group consisting of alkyl, alkenyl, cycloalkyl and phenyl, X is halogen and $n$ is an integer from 1 to 2, (2) a monoepoxide selected from the group consisting of a styrene oxide and an epoxide of the formula

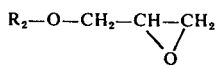

wherein $R_2$ is an organic group selected from the group consisting of phenyl and amino, halo and alkyl substituted phenyl, alkyl, alkenyl and a group having the formula

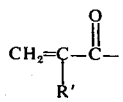

wherein R′ is hydrogen or methyl, and (3) a diepoxide selected from the group consisting of a diepoxide of the formula

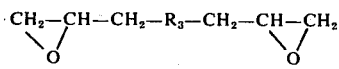

wherein $R_3$ is a divalent organic group selected from the group consisting of alkylene, alkyleneoxyalkylene, oxyalkyleneoxy, oxyalkyleneoxyalkyleneoxy, a group of the formula

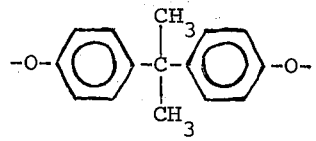

and a group of the formula

and a cyclohexane diepoxide, with the diepoxide being reacted in an amount less than two epoxide equivalents based upon a mole of silane.

16. Compounds as defined in claim 15 wherein the reaction mixture includes 0.5 to 2 epoxide equivalents of the monoepoxide and 1 to 2 epoxide equivalents of the diepoxide per mole of halosilane.

17. Compounds as defined in claim 15 wherein the reaction mixture includes 1 to 2 moles of an alkylene oxide and/or a monohydric alcohol per mole of halosilane.

18. A compound selected from the group consisting of a compound of the formula

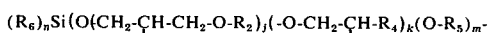

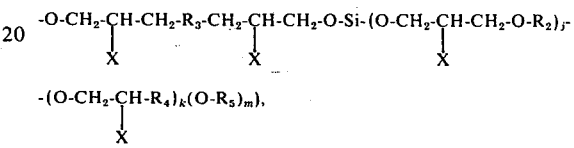

a compound of the formula

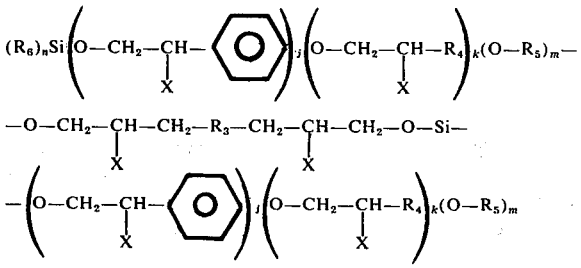

and mixtures thereof, wherein $R_2$ is an organic group selected from the group consisting of phenyl and amino, halo and alkyl substituted phenyl, alkyl, alkenyl and a group having the formula

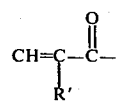

wherein R′ is hydrogen or methyl, X is halogen, $R_4$ is alkyl or hydrogen, $R_5$ is selected from the group consisting of alkyl, alkenyl, benzyl and aminoalkyl, $R_3$ is a divalent organic group consisting of alkylene, alkyleneoxyalkylene, oxyalkyleneoxy, oxyalkyleneoxyalkyleneoxy, a group of the formula

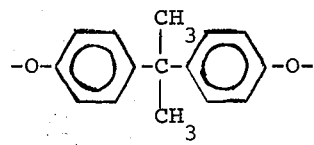

and a group of the formula

wherein *j* is an integer from 1 to 2 where *n* is 1 and *j* is 1 where *n* is 2, and *k* is 0 or 1 and *m* is 0 or 1.
19. A compound of the formula
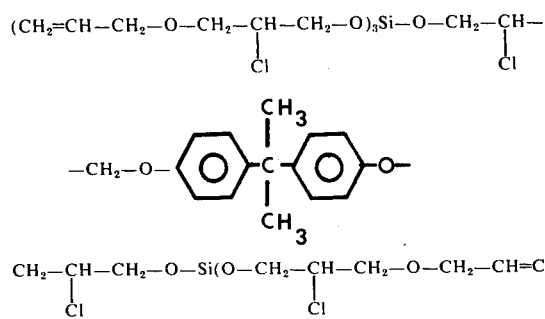
20. Organo silicon compounds prepared by reaction of silicon tetrachloride, allyl glycidyl ether and an epoxide of the formula
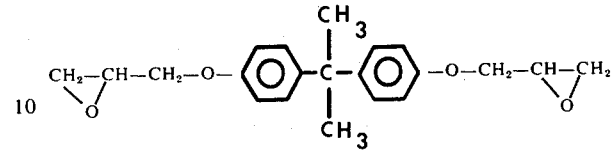
with the epoxide being reacted in an amount less than two epoxide equivalents per mole of silicon tetrachloride.
* * * * *